US011242512B2

(12) United States Patent
Iyidogan

(10) Patent No.: US 11,242,512 B2
(45) Date of Patent: Feb. 8, 2022

(54) ENGINEERED POLYMERASES FOR IMPROVED SEQUENCING

(71) Applicant: OMNIOME, INC., San Diego, CA (US)

(72) Inventor: Pinar Iyidogan, San Diego, CA (US)

(73) Assignee: OMNIOME, INC., San Diego, CA (US)

( * ) Notice: Subject to any disclaimer, the term of this patent is extended or adjusted under 35 U.S.C. 154(b) by 0 days.

(21) Appl. No.: 16/567,476

(22) Filed: Sep. 11, 2019

(65) Prior Publication Data

US 2020/0087637 A1    Mar. 19, 2020

Related U.S. Application Data

(60) Provisional application No. 62/732,510, filed on Sep. 17, 2018.

(51) Int. Cl.
| C12N 9/12 | (2006.01) |
| C12P 19/34 | (2006.01) |
| C12Q 1/6874 | (2018.01) |

(52) U.S. Cl.
CPC ......... *C12N 9/1252* (2013.01); *C12N 9/1276* (2013.01); *C12P 19/34* (2013.01); *C12Q 1/6874* (2013.01); *C12Y 207/07007* (2013.01); *C12Y 207/07049* (2013.01)

(58) Field of Classification Search
CPC combination set(s) only.
See application file for complete search history.

(56) References Cited

U.S. PATENT DOCUMENTS

| 7,057,026 | B2 | 6/2006 | Barnes et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,414,116 | B2 | 8/2008 | Milton et al. |
| 7,427,673 | B2 | 9/2008 | Balasubramanian et al. |
| 7,544,794 | B1 | 6/2009 | Benner et al. |
| 7,871,771 | B2 | 1/2011 | Fuller et al. |
| 7,956,171 | B2 | 6/2011 | Siddiqi et al. |
| 8,034,923 | B1 | 10/2011 | Benner et al. |
| 8,071,755 | B2 | 12/2011 | Efcavitch et al. |
| 8,399,196 | B2 | 3/2013 | Hoser |
| 8,460,910 | B2 | 6/2013 | Smith et al. |
| 8,772,006 | B2 | 7/2014 | Sorge et al. |
| 8,808,989 | B1 | 8/2014 | Siddiqi et al. |
| 9,399,767 | B2 | 7/2016 | Peris et al. |
| 9,399,798 | B2 | 7/2016 | Morris et al. |
| 9,593,315 | B2 | 3/2017 | Peris et al. |
| 9,765,310 | B2 | 9/2017 | Vander Horn et al. |
| 9,951,385 | B1 | 4/2018 | Vijayan et al. |
| 10,161,003 | B2 | 12/2018 | Stromberg et al. |
| 10,400,272 | B1 | 9/2019 | Middleton et al. |
| 2008/0108082 | A1 | 5/2008 | Rank et al. |
| 2016/0362664 | A1* | 12/2016 | Smith ............... C12Q 1/6869 |
| 2017/0022553 | A1 | 1/2017 | Vijayan et al. |
| 2017/0314072 | A1 | 11/2017 | Vijayan et al. |
| 2018/0044715 | A1 | 2/2018 | Iyidogan et al. |
| 2018/0044727 | A1 | 2/2018 | Vijayan et al. |
| 2018/0119115 | A1 | 5/2018 | Lin Wu et al. |
| 2018/0155698 | A1 | 6/2018 | Iyidogan et al. |
| 2018/0187245 | A1 | 7/2018 | Dambacher et al. |
| 2018/0208983 | A1 | 7/2018 | Dambacher et al. |
| 2019/0119740 | A1 | 4/2019 | Ahn et al. |

FOREIGN PATENT DOCUMENTS

| WO | 91/06678 A1 | 5/1991 |
| WO | 03054139 | 7/2003 |
| WO | 2005024010 | 3/2005 |
| WO | 2006037064 | 4/2006 |
| WO | 2006120433 | 11/2006 |
| WO | 2007/123744 A2 | 11/2007 |
| WO | 2008079765 A1 | 7/2008 |
| WO | 2009131919 | 10/2009 |
| WO | 2011135280 A1 | 11/2011 |
| WO | 2012154934 A1 | 11/2012 |
| WO | 2014142921 | 9/2014 |
| WO | 2016054096 A1 | 4/2016 |
| WO | 2017042040 | 3/2017 |
| WO | 2018148727 | 8/2018 |

OTHER PUBLICATIONS

U.S. Appl. No. 16/567,598, Final Office Action, dated May 5, 2020, 7 pages.
Athey et al., "A new and updated resource for codon usage tables", BMC Bioinformatics 18(1), 2017, pp. 391-401.
Chen et al., "The History and Advances of Reversible Terminators Used in New Generations of Sequencing Technology", Genomics Proteomics Bioinformatics, vol. 11, Issue 1, Feb. 1, 2013, pp. 34-40.
Delarue et al., "An attempt to unify the structure of polymerases", Protein Engineering, vol. 3, 1990, pp. 461-467.
Doublie et al., "Crystal structure of a bacteriophage T7 DNA replication complex at 2.2 A resolution", Nature, vol. 391, Jan. 1998, pp. 251-258.
Gardner et al., "Acyclic and dideoxy terminator preferences denote divergent sugar recognition by archaean and Taq DNA polymerases", Nucleic Acids Research, vol. 30, No. 2, 2002, pp. 605-613.

(Continued)

*Primary Examiner* — Richard G Hutson
(74) *Attorney, Agent, or Firm* — Kilpatrick Townsend & Stockton LLP

(57) ABSTRACT

Provided are nucleic acids encoding engineered polymerases comprising at least one modification in a motif A and/or at least one modification in a motif B of the polymerase and engineered polymerases encoded by the nucleic acids. Also provided are engineered DNA polymerases comprising a variant of SEQ ID NO:1, SEQ ID NO:2, or SEQ ID NO:3, the variant being at least 80% identical to SEQ ID NO:1, SEQ ID NO:2 or SEQ ID NO:3 and comprising an amino acid substitution at one or more positions selected from the group consisting of L408, Y409, P410, R484, A/L485, and I486. Methods, vectors, kits, and compositions comprising the nucleic acids and compositions, methods and kits comprising the engineered polymerases are also provided.

14 Claims, 3 Drawing Sheets

Specification includes a Sequence Listing.

(56) References Cited

OTHER PUBLICATIONS

Kropp et al., "Crystal structures of ternary complexes of archaeal B-family DNA polymerases", PloS one 12.12: e0188005, 2017, 20 pages.
Pelletier et al., "Structures of ternary complexes of rat DNA polymerase beta, a DNA template-primer, and ddCTP", Science 264(5167), 1994, pp. 1891-1903.
Shinkai et al., "The Conserved Active Site Motif A of *Escherichia coli* DNA Polymerase I Is Highly Mutable", Journal of Biological Chemistry 276(22), 2001, p. 18836-18842.
Steitz, Thomas, "DNA polymerases: structural diversity and common mechanisms", Journal of Biological Chemistry 274(25), 1999, p. 17395-17398.
"9degreeN DNA Polymerase Variant #3", XP002797079, Retrieved from EBI Accession No. GSP:ADY63797, Database Accession No. ADY63797, Jun. 2, 2005, 2 pages.
Gardner et al., "Rapid Incorporation Kinetics and Improved Fidelity of a Novel Class of 3'-OH Unblocked Reversible Terminators", Nucleic Acids Research, vol. 40, No. 15, Aug. 1, 2012, pp. 7404-7415.
GB1913100.2, "Combined Search and Examination Report", dated Oct. 28, 2019, 10 pages.
Likui et al., "Archaeal DNA Polymerases in Biotechnology", Applied Microbiology and Biotechnology, vol. 99, No. 16, Jul. 7, 2015, pp. 6585-6597.
PCT/US2019/050535, "Invitation to Pay Additional Fees and, Where Applicable, Protest Fee", Nov. 11, 2019, 13 pages.
U.S. Appl. No. 16/567,598, "Non-Final Office Action", 11 pages.
PCT/US2019/050535, "International Search Report and Written Opinion", dated Feb. 10, 2020, 22 pages.

* cited by examiner

ENGINEERED POLYMERASES FOR IMPROVED SEQUENCING

CROSS REFERENCE TO RELATED APPLICATION

This application claims priority to U.S. Provisional Application No. 62/732,510, filed Sep. 17, 2018, which is incorporated by reference herein in its entirety.

BACKGROUND

Naturally occurring DNA polymerizing enzymes are responsible for accurately replicating DNA within the cells of an organism. This process involves catalysis at the 3'-end of a growing DNA strand, whereby a free deoxyribonucleotide triphosphate (dNTP) having a base moiety matched to the base moiety on the complementary template strand is incorporated. This requirement for complementarity is utilized by sequencing technologies to analyze DNA for medical, industrial, and scientific applications.

DNA polymerases are important tools for determining identity of the next correct nucleotide (i.e., the "cognate" nucleotide) of a template nucleic acid, whether for detection of single nucleotide polymorphisms (SNPs) or more extensive sequence determination. Example applications include sequencing by synthesis technology, where cognate nucleotide identification follows nucleotide incorporation; and Sequencing By Binding™ technology, where cognate nucleotide identification is based on observations or measurements of binding events taking place prior to, or without, nucleotide incorporation. Given the utility and advantages of sequencing, there is an ongoing need for new and useful tools and methods that can be used for enhancing discrimination between cognate and non-cognate nucleotide in the sequencing procedure.

BRIEF SUMMARY

Provided are nucleic acids encoding engineered polymerases comprising at least one modification in a motif A and/or at least one modification in a motif B of the polymerase and engineered polymerases encoded by the nucleic acids. Also provided are engineered DNA polymerases comprising a variant of SEQ ID NO:1, SEQ ID NO:2, or SEQ ID NO:3, the variant being at least 80% identical to SEQ ID NO:1, SEQ ID NO:2 or SEQ ID NO:3 and comprising an amino acid substitution at one or more positions selected from the group consisting of L408, Y409, P410, R484, A/L485, and I486. Methods, vectors, kits, and compositions comprising the nucleic acids and compositions, methods and kits comprising the engineered polymerases are also provided.

DETAILED DESCRIPTION

Figure 1:
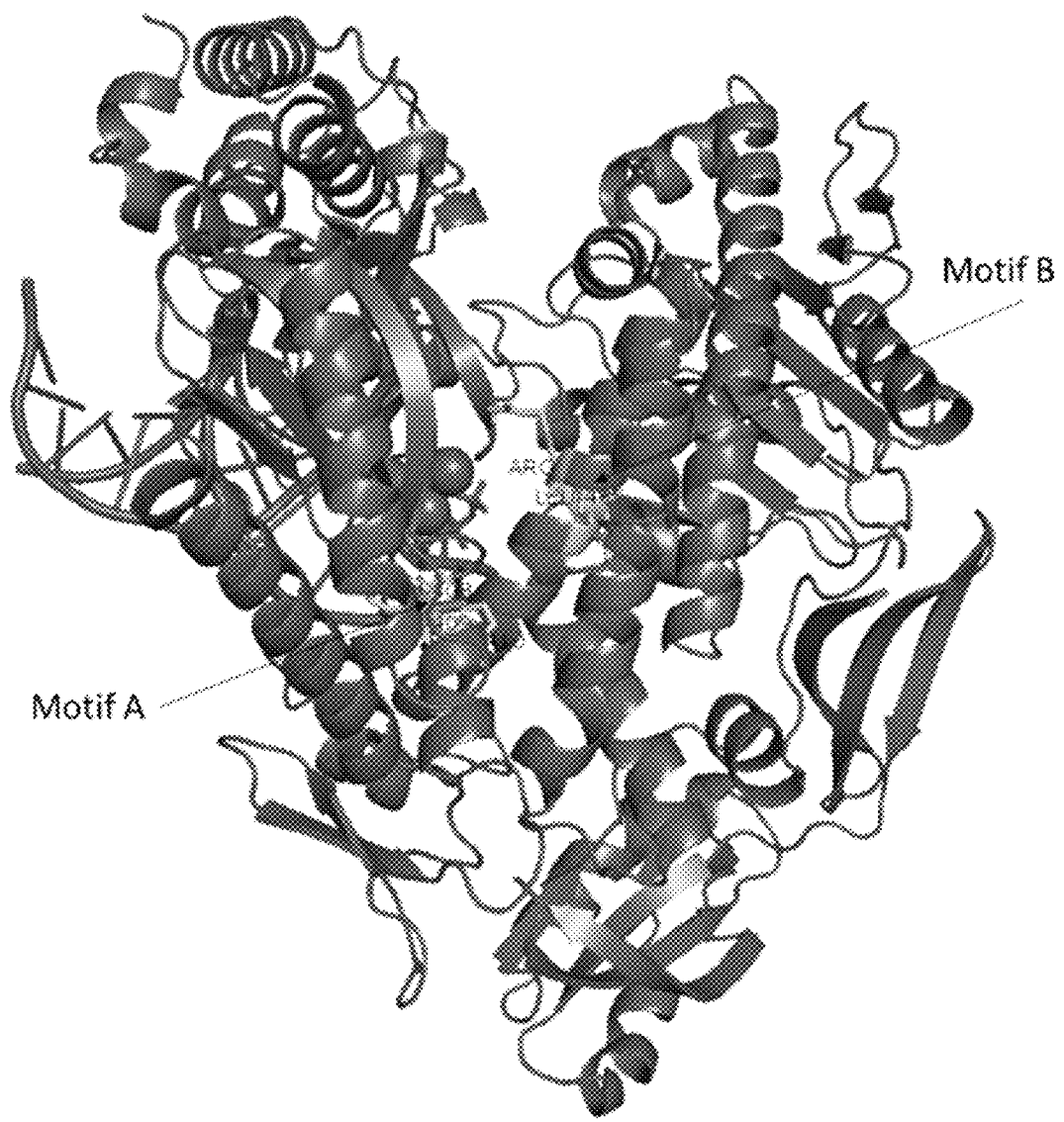
FIG. 1 is a schematic showing the crystal structure of 9° N DNA polymerase and showing Motif A and Motif B of the polymerase.

Sequencing By Binding™ technology in various embodiments, including but not limited to those disclosed by Vijayan et al., in U.S. Pat. App. Pub. Nos. 2017/0022553 A1 or 2018/0044727 A1, or U.S. Pat. No. 9,951,385, each of which is incorporated by reference herein, benefits from reduced polymerase binding to a primed template nucleic acid in the absence of cognate nucleotide (e.g., whether in the absence of any nucleotide, or in the presence of only non-cognate nucleotide). Different approaches have proven useful for reducing the magnitude of this binary complex formation, while at the same time stabilizing ternary complexes that include primed template nucleic acid, polymerase, and the cognate nucleotide. For example, some approaches rely on manipulation of salt concentrations or the manner of delivering polymerase to the primed template to enhance this discrimination.

Polymerases that exhibit better enzymatic properties like increased accuracy in pairing nucleotides to template bases, increased stability, improved polymerization kinetic rates, and decreased polymerization error rates as compared to a control polymerase would be useful tools in sequencing methods like Sequencing By Binding™ methods. Described herein are engineered polymerases that are useful for such sequencing procedures and processes. The engineered polymerases can have other uses as will be recognized by those skilled in the art in view of the teaching set forth herein.

Definitions

Unless defined otherwise, all technical and scientific terms used herein have the same meaning as is commonly understood by one of ordinary skill in the art. For clarity, the following specific terms have the specified meanings. Other terms are defined in other sections herein.

The singular forms "a" "an" and "the" include plural referents unless the context clearly dictates otherwise. Approximating language, as used in the description and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the compositions, apparatus, or methods of the present disclosure. At the very least, each numerical parameter should at least be construed in light of the number of reported significant digits and by applying ordinary rounding techniques.

As used herein, "nucleic acid" or "oligonucleotide" or "polynucleotide" or grammatical equivalents used herein means at least two nucleotides covalently linked together. Thus, an exemplary "nucleic acid" is a polynucleotide, such as DNA, RNA, or any combination thereof, that can be acted upon by a polymerizing enzyme during nucleic acid synthesis. The term "nucleic acid" includes single-, double-, or multiple-stranded DNA, RNA and analogs (derivatives) thereof. Double-stranded nucleic acids advantageously can minimize secondary structures that may hinder nucleic acid synthesis. A double stranded nucleic acid may possess a nick or a single-stranded gap.

As used herein, the "next correct nucleotide" is the nucleotide having a base complementary to the base of the next template nucleotide. The next correct nucleotide can be referred to as a "cognate" of the next template nucleotide and vice versa. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. The next correct nucleotide can be a nucleotide analog. A nucleotide having a base that is not complementary to the next template base is referred to as an "incorrect" (or "non-cognate") nucleotide. The next correct nucleotide, when participating in a ternary complex, is non-covalently bound to the primed template nucleic acid of the ternary complex.

As used herein, the "next template nucleotide" refers to the next nucleotide in a template nucleic acid that pairs with a position that is located immediately downstream of the 3'-end of a hybridized primer. In other words, the next template nucleotide is located immediately 5' of the base in the template that is hybridized to the 3' end of the primer. The base moiety of the next template nucleotide is referred to as the "next template base".

As used herein, a "template nucleic acid" is a nucleic acid to be acted upon (e.g., amplified, detected or sequenced) using a method or composition disclosed herein.

As used herein, a "primed template nucleic acid," "primed template nucleic acid molecule," or "primer-template nucleic acid hybrid" is a template nucleic acid primed with (i.e., hybridized to) a primer, wherein the primer is an oligonucleotide having a 3'-end with a sequence complementary to a portion of the template nucleic acid. The primer can optionally have a free 5'-end (e.g., the primer being noncovalently associated with the template) or the primer can be continuous with the template (e.g., via a hairpin structure). The primed template nucleic acid includes the complementary primer and the template nucleic acid to which it is bound. Unless explicitly stated, the primer of the primed template nucleic acid can have either a 3'-end that is extendible by a polymerase, or a 3'-end that is blocked from extension.

As used herein, a "blocked primed template nucleic acid" (or alternatively, "blocked primed template nucleic acid molecule") is a primed template nucleic acid modified to preclude or prevent phosphodiester bond formation at the 3'-end of the primer. Blocking may be accomplished, for example, by chemical modification with a blocking group at either the 3' or 2' position of the five-carbon sugar at the 3' terminus of the primer. Alternatively, or in addition, chemical modifications that preclude or prevent phosphodiester bond formation may also be made to the nitrogenous base of a nucleotide. Reversible terminator nucleotide analogs including each of these types of blocking groups will be familiar to those having an ordinary level of skill in the art. Incorporation of these analogs at the 3' terminus of a primer of a primed template nucleic acid molecule results in a blocked primed template nucleic acid molecule. The blocked primed template nucleic acid includes the complementary primer, blocked from extension at its 3'-end, and the template nucleic acid to which it is bound.

As used herein, a "nucleotide" is a molecule that includes a nitrogenous base, a five-carbon sugar (ribose or deoxyribose), and at least one phosphate group. The term embraces, but is not limited to, ribonucleotides, deoxyribonucleotides, nucleotides modified to include exogenous labels or reversible terminators, and nucleotide analogs.

As used herein, a "native" nucleotide refers to a naturally occurring nucleotide that does not include an exogenous label (e.g., a fluorescent dye, or other label) or chemical modification such as may characterize a non-natural nucleotide analog. Examples of native nucleotides useful for carrying out the Sequencing By Binding™ procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, a "non-natural nucleotide analog" has one or more modifications, such as chemical moieties, which replace, remove and/or modify any of the components (e.g., nitrogenous base, five-carbon sugar, or phosphate group(s)) of a native nucleotide. Non-natural nucleotide analogs may be either incorporable or non-incorporable by a polymerase in a nucleic acid polymerization reaction. Optionally, the 3'-OH group of a non-natural nucleotide analog is modified with a moiety. The moiety may be a reversible or irreversible terminator of polymerase extension. The base of a nucleotide, whether it be a native nucleotide or non-natural nucleotide analog, may be any of adenine, cytosine, guanine, thymine, or uracil, or analogs thereof. Optionally, a nucleotide has an inosine, xanthine, hypoxanthine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dUTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP, ddUTP and ddCTP).

As used herein, a "blocking moiety," when used with reference to a nucleotide, is a part of the nucleotide that inhibits or prevents the nucleotide from forming a covalent linkage to a second nucleotide (e.g., via the 3'-OH of a primer nucleotide) during the incorporation step of a nucleic acid polymerization reaction. The blocking moiety of a "reversible terminator" nucleotide can be modified or removed from the nucleotide to allow for nucleotide incorporation. Such a blocking moiety is referred to herein as a "reversible terminator moiety." Exemplary reversible terminator moieties are set forth in U.S. Pat. Nos. 7,427,673; 7,414,116; and 7,057,026 and PCT publications WO 91/06678 and WO 07/123744, each of which is incorporated by reference.

As used herein, a "test nucleotide" is a nucleotide being investigated for its ability to participate in formation of a ternary complex that further includes a primed template nucleic acid and a polymerase.

As used herein, "polymerase" refers to a protein or other molecule that forms a ternary complex with a cognate nucleotide and primed template nucleic acid (e.g. blocked primed template nucleic acid), including but not limited to, DNA polymerase, RNA polymerase, reverse transcriptase, primase and transferase. Typically, the polymerase includes one or more active sites at which nucleotide binding and/or catalysis of nucleotide polymerization may occur. The polymerase may catalyze the polymerization of nucleotides to the 3'-end of a primer bound to its complementary nucleic acid strand. For example, a polymerase can catalyze the addition of a next correct nucleotide to the 3' oxygen of the primer via a phosphodiester bond, thereby chemically incorporating the nucleotide into the primer. Optionally, a polymerase used in the provided methods is a processive polymerase. Optionally, a polymerase used in the provided methods is a distributive polymerase. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, a "variant" of a polypeptide reference sequence is a form or version of the polypeptide sequence that differs in some respect. Variants can differ in amino acid sequence and can include, for example, amino acid substitutions, additions (e.g., insertions, and extensions of termini), and deletions. A variant of a polypeptide reference sequence can include amino acid substitutions and/or internal additions and/or deletions and/or additional amino acids at one or both termini of the reference sequence.

As used herein, a "polyhistidine-tag motif" is an amino acid motif in proteins that consists of six or more contiguous histidine residues, and that facilitates binding of the proteins to divalent nickel ions. For example, a polyhistidine-tag motif can bind to an affinity support (e.g., bead or resin) containing bound divalent nickel ions.

As used herein, a "salt providing monovalent cation" is an ionic compound that dissociates in aqueous solution to produce cations having a single positive charge. For example, the cations can be metal cations where the oxidation state is +1.

As used herein, "a glutamate salt" is an ionic compound that dissociates in aqueous solution to produce glutamate anions.

As used herein, "providing" a template, a primer, a primed template nucleic acid (e.g. a blocked primed template nucleic acid) refers to the delivery of one or many nucleic acid polymers, for example to a reaction mixture or reaction chamber. Optionally, providing a material can include preparation of the material in addition to its delivery.

As used herein, "monitoring" refers to a process of examining for a detectable phenomenon, wherein the phenomenon may or may not occur. In some cases, monitoring can entail detecting a measurable interaction or binding between two molecular species. For example, monitoring may involve detecting measurable interactions between a polymerase and primed template nucleic acid, typically at various points throughout a procedure. Monitoring can be intermittent (e.g., periodic) or continuous (e.g., without interruption), and can involve acquisition of quantitative results. Monitoring can be carried out by detecting multiple signals over a period of time during a binding event or, alternatively, by detecting signal(s) at a single time point during or after a binding event.

As used herein, "contacting," when used in reference to reagents, refers to the mixing together of the reagents (e.g., mixing an immobilized template nucleic acid and either a buffered solution that includes a polymerase, or the combination of a polymerase and a test nucleotide) so that a physical binding reaction or a chemical reaction may take place.

As used herein, "incorporating" or "chemically incorporating," when used in reference to a primed template and nucleotide, refers to the process of joining a cognate nucleotide to a primer by formation of a phosphodiester bond.

As used herein, "extension" refers to the process after an oligonucleotide primer and a template nucleic acid have annealed to one another, one or more nucleotides is added at the 3'-end of the primer. A polymerase enzyme can catalyze addition of a single nucleotide to a primer. An oligonucleotide, which contains multiple nucleotides, can be added to a primer by a ligase enzyme. A nucleotide or oligonucleotide that is added to a nucleic acid by extension is said to be "incorporated" into the nucleic acid. Accordingly, the term "incorporating" can be used to refer to the process of joining a nucleotide to the 3'-end of a primer by formation of a phosphodiester bond.

As used herein, a "binary complex" is an intermolecular association between a polymerase and a primed template nucleic acid (e.g., blocked primed template nucleic acid), where the complex does not include a nucleotide molecule such as the next correct nucleotide.

As used herein, a "ternary complex" is an intermolecular association between a polymerase, a primed template nucleic acid (e.g., blocked primed template nucleic acid), and the next correct nucleotide molecule positioned immediately downstream of the primer and complementary to the template strand of the primed template nucleic acid or the blocked primed template nucleic acid. The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation). The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, a "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at sufficiently low concentrations to stabilize formation of a complex between a polymerase, a nucleotide, and a primed template nucleic acid, referred to as non-catalytic concentrations of a metal ion. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, a "non-catalytic metal ion" refers to a metal ion that, when in the presence of a polymerase enzyme, does not facilitate phosphodiester bond formation needed for chemical incorporation of a nucleotide into a primer. Typically, the non-catalytic metal ion is a cation. A non-catalytic metal ion may inhibit phosphodiester bond formation by a polymerase, and so may stabilize a ternary complex by preventing nucleotide incorporation. Non-catalytic metal ions may interact with polymerases, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein an "exogenous label" refers to a detectable chemical moiety of a molecule (e.g. a sequencing reagent) that is not present in a natural analog of the molecule, such as a non-naturally occurring label present on a synthetic nucleotide or synthetic polymerase. While a native dNTP may have a characteristic limited fluorescence profile, the native dNTP does not include any added colorimetric or fluorescent moiety. Conversely, a dATP (2'-deoxyadenosine-5'-triphosphate) molecule modified to include a chemical linker and fluorescent moiety attached to the gamma phosphate would be said to include an exogenous label because the attached chemical components are not ordinarily a part of the nucleotide. Of course, chemical modifications to add detectable labels to nucleotide bases also would be considered exogenous labels. Likewise, a DNA polymerase modified to include a fluorescent dye also would be said to include an exogenous label because the label is not ordinarily a part of the polymerase.

As used herein, "unlabeled" refers to a molecular species free of added or exogenous label(s) or tag(s). Of course, unlabeled nucleotides will not include either of an exogenous fluorescent label, or an exogenous Raman scattering tag. A native nucleotide is another example of an unlabeled molecular species. An unlabeled molecular species can exclude one or more of the labels set forth herein or otherwise known in the art relevant to nucleic acid sequencing or analytical biochemistry.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, a "flow cell" is a reaction chamber that includes one or more channels that direct fluid in a predetermined manner to conduct a desired reaction. The flow cell can be coupled to a detector such that a reaction occurring in the reaction chamber can be observed. For example, a flow cell can contain primed template nucleic acid molecules, for example, tethered to a solid support, to which nucleotides and ancillary reagents are iteratively applied and washed away. The flow cell can include a transparent material that permits the sample to be imaged after a desired reaction occurs. For example, a flow cell can include a glass or plastic slide containing small fluidic channels through which polymerases, dNTPs and buffers can be pumped. The glass or plastic inside the channels can be decorated with one or more primed template nucleic acid molecules to be sequenced. An external imaging system can be positioned to detect the molecules on the surface of the glass or plastic. Reagent exchange in a flow cell is accomplished by pumping, drawing, or otherwise "flowing" different liquid reagents through the flow cell. Exemplary flow cells, methods for their manufacture and methods for their use are described in US Pat. App. Publ. Nos. 2010/0111768 A1 or 2012/0270305 A1; or WO 05/065814, each of which is incorporated by reference herein.

As used herein, a "reaction vessel" is a container that isolates one reaction (e.g., a binding reaction; an incorporation reaction; etc.) from another, or that provides a space in which a reaction can take place. Non-limiting examples of reaction vessels useful in connection with the disclosed technique include: flow cells, wells of a multiwell plate; microscope slides; tubes (e.g., capillary tubes); etc. Features to be monitored during binding and/or incorporation reactions can be contained within the reaction vessel.

As used herein, a "kit" is a packaged unit containing one or more components that can be used for performing detection and/or sequencing reactions using an engineered polymerase, as disclosed herein. Typical kits may include packaged combinations, in one or more containers or vials, of reagents to be used in the procedure and instructions for use.

As used herein, "motif A" refers to the conserved region among polymerases involved in nucleotide binding and substrate specificity. Optionally, motif A refers specifically to a motif that includes amino acids 408-410 of the polymerases in SEQ ID Nos: 1, 2 or 3.

As used herein, "motif B" refers to the conserved region among polymerases involved in nucleotide binding. Optionally, motif B refers specifically to a motif that includes amino acids 484-486 of the polymerases in SEQ ID Nos: 1, 2 or 3.

The terms "motif A" and "motif B" are intended to be used in accordance with their known meaning in the art, wherein the terms are used to refer to regions of structural homology in the nucleotide binding sites of B family and other polymerases. DNA polymerases have a common overall structure that has been likened to a human right hand, with fingers, thumb, and palm subdomains. The palm subdomain contains motif A which in turn contains a catalytically essential aspartic acid residue. In native DNA polymerases, motif A begins at an anti-parallel β-strand containing predominantly hydrophobic residues and is followed by a turn and an α-helix. In native DNA polymerases, motif A interacts with a next correct nucleotide via coordination with divalent metal ions that participate in the polymerization reaction. Motif B contains an alpha-helix with positive charges. Further characteristics of motif A and motif B are known in the art, for example, as set forth in Delarue et al. *Protein Eng.* 3: 461-467 (1990); Shinkai et al. *J. Biol. Chem.* 276: 18836-18842 (2001) and Steitz *J. Biol. Chem.* 274: 17395-17398 (1999), each of which is incorporated herein by reference. Functionally equivalent or homologous "motif A" and "motif B" regions of polymerases other than the ones described herein can be identified on the basis of amino acid sequence alignment and/or molecular modelling. Sequence alignments may be compiled using any of the standard alignment tools known in the art, such as for example BLAST and the like.

As used herein, "increased stability" in reference to an engineered polymerase refers to the engineered polymerase having increased stability relative to a parental, control polymerase. Stability includes thermostability, increased ternary complex stability, increased half-life and the like.

As used herein, "improved polymerization kinetic rates" in reference to an engineered polymerase means the engineered polymerase has improved polymerization kinetic rates relative to a parental, control polymerase. In other words, the engineered polymerase performs better than the parental, control polymerase in one or more ways. Performance can be based on known parameters, including but not limited to, on rate ($k_{on}$), off rate ($k_{off}$), dissociation constant ($K_D$), turnover number ($k_{cat}$) and the Michaelis constant ($K_M$). The formation and stability of binary and ternary complexes can be predicted from the kinetic rates (e.g. $k_{on}$, $k_{off}$) and the dissociation constants ($K_D$) of polymerase, template DNA, and dNTPs, respectively. Enzymatic parameters $k_{cat}$ and $K_M$, which can be determined by $(k_{off}+k_{cat})/k_{on}$, can also be used to compare performances of different polymerases.

As used herein, "decreased polymerization error rates" in reference to an engineered polymerase means the engineered polymerase is less likely to incorporate an incorrect nucleotide into a template during a sequencing process as compared to a parental, control polymerase.

"Control polymerase" is defined herein as the polymerase against which the activity of the altered polymerase is compared. Optionally, the control polymerase may comprise a wild type polymerase or an exo-variant thereof. Unless otherwise stated, by "wild type" it is generally meant that the polymerase comprises its natural amino acid sequence, as it would be found in nature. Optionally, the control polymerase has the amino acid sequence of SEQ ID NO:1, SEQ ID NO:2 or SEQ ID NO:3. A control polymerase can differ from an altered polymerase at one or more amino acid positions. For example, at least 1, 2, 3, 4, 5, 6, 7, 8 or 9 positions can differ between the control polymerase and the altered polymerase. Alternatively or additionally, no more than 10, 9, 8, 7, 6, 5, 4, 3, 2, or 1 positions can differ between the control polymerase and the altered polymerase. The positions that differ can include one or more of those identified herein, for example, in Table 1.

As used herein, "thermostable" refers to a property of a polymerase, such that the enzyme active at elevated temperatures and is resistant to DNA duplex-denaturing temperatures in the range of about 93° C. to about 97° C. "Active" means the enzyme retains the ability to effect primer extension reactions when subjected to elevated or denaturing temperatures for the time necessary to effect denaturation of double-stranded nucleic acids. Elevated temperatures as used herein can refer to the range of about 70° C. to about 75° C., whereas non-elevated temperatures as used herein can refer to the range of about 25° C. to about 50° C.

Nucleic Acids Encoding Engineered Polymerases

Provided herein are nucleic acids encoding an engineered polymerase comprising at least one modification in a motif A and/or at least one modification in a motif B of the polymerase. Optionally, the engineered polymerase comprises at least one modification in a motif A and at least one modification in a motif B. Optionally, motif A comprises a modification at amino acid position L408, Y409, P410, or any combination thereof. Optionally, motif A comprises modifications at amino acid positions L408 and Y409; L408 and P410; Y409 and P410; or L408, Y409 and P410. Modifications to motif A include, but are not limited to, L408F, Y409F, Y409H, P410T, P410V, or any combination thereof. Optionally, modifications in motif A are L408F/Y409F/P410T or L408F/Y409H/P410V.

Motif B can also include one or more modifications. Optionally, motif B comprises a modification at amino acid position R484, A/L485, I486, or any combination thereof. Optionally, when the modification is A485, the polymerase further includes at least one additional modification in motif A and/or motif B. Optionally, when the modification is A485, the polymerase is not the 9° N polymerase. Optionally, motif B comprises modifications at amino acid positions R484 and A/L485; R484 and I486; A/L485 and I486; or R484, A/L485 and I486. Modifications to motif B include, but are not limited to, R484F, R484I, A/L485H, R484A, R484L, R484S, R484Q, R484T, R484K, R484, A/L485K, A/L485H, A/L485D, A/L485T, A/L485N, A/L485W, A/L485F, I486L, I486V, I486R, I486H, I486F, I486G, or any combination thereof. Optionally, the modifications in motif B are I486V, R484F/I486L, R484I/A/L485K/I486R, A/L485H/I486H, R484A/A/L485D/I486R, R484L, R484S/A/L485T/I486L, R484Q/A/L485T/I486L, R484Q/A/L485T/I486L, R484Q/A/L485T/I486F, R484T/I486V, R484K/A/L485T/I486F, R484L/A/L485N/I486R, A/L485W/I486G, R484L/I486V, or R484S/A/L485F/I486R.

As discussed throughout, an engineered polymerase can include any combination of modifications at positions L408, Y409, P410, R484, A/L485, and I486. Table 1 lists the possible modifications the engineered polymerases can include. Modifications to motif A are listed in the first column and modifications to motif B are listed in the second column. Each row in Table 1 identifies a combination of positions, including both motif A positions and motif B positions, that can be modified in a particular polymerase molecule.

TABLE 1

List of Polymerase Modifications.

| Motif A Amino Acid Position | Motif B Amino Acid Position |
| --- | --- |
| None | R484; A/L485; I486; or any combination thereof |
| L408; Y409; P410; or any combination thereof | None |
| L408 | R484 |
| L408 | A/L485 |
| L408 | I486 |
| Y409 | R484 |
| Y409 | A/L485 |
| Y409 | I486 |
| P410 | R484 |
| P410 | A/L485 |
| P410 | I486 |
| L408 | R484; A/L485 |
| L408 | R484; I486 |
| L408 | A/L485; I486 |
| Y409 | R484; A/L485 |
| Y409 | R484; I486 |
| Y409 | A/L485; I486 |
| P410 | R484; A/L485 |
| P410 | R484; I486 |
| P410 | A/L485; I486 |
| L408 | R484; A/L485; I486 |
| Y409 | R484; A/L485; I486 |
| P410 | R484; A/L485; I486 |
| L408; Y409 | R484 |
| L408; Y409 | A/L485 |
| L408; Y409 | I486 |
| L408; Y409 | R484; A/L485 |
| L408; Y409 | R484; I486 |
| L408; Y409 | A/L485; I486 |
| L408; Y409 | R484; A/L485; I486 |
| L408; P410 | R484 |
| L408; P410 | A/L485 |
| L408; P410 | I486 |
| L408; P410 | R484; A/L485 |
| L408; P410 | R484; I486 |
| L408; P410 | A/L485; I486 |
| L408; P410 | R484; A/L485; I486 |
| Y409; P410 | R484 |
| Y409; P410 | A/L485 |
| Y409; P410 | I486 |
| Y409; P410 | R484; A/L485 |
| Y409; P410 | R484; I486 |
| Y409; P410 | A/L485; I486 |
| Y409; P410 | R484; A/L485; I486 |
| L408; Y409; P410 | R484 |
| L408; Y409; P410 | A/L485 |
| L408; Y409; P410 | I486 |
| L408; Y409; P410 | R484; A/L485 |
| L408; Y409; P410 | R484; I486 |
| L408; Y409; P410 | A/L485; I486 |
| L408; Y409; P410 | R484; A/L485; I486 |

The engineered polymerases may also include a modification at amino acid position D141 and/or E143. Optionally, the modifications are D141A and E143A. Optionally, the engineered polymerases further include a modification at amino acid position K240, e.g., K240R.

The amino acid positions in Table 1 are numbered relative to SEQ ID NO:1, 2 or 3. Motifs A and B are highly conserved among polymerases. Thus, they can be defined in terms of primary structure (e.g. amino acid sequence) or tertiary structure (e.g. crystal structure). See, for example, Kropp, et al., "Crystal structures of ternary complexes of archael B-family DNA polymerases" PLOS One 12(12): e0188005 (2017). A polymerase of the present disclosure can include modification(s) at one or more positions in motif A or motif B that are homologous to the positions exemplified herein with respect to SEQ ID NO: 1, 2 or 3, such as the positions listed in Table 1. Modifications in motif A include, but are not limited to, modifications in amino acids located from 2.5 to 4.5 angstroms from the 3'OH group when nucleotide is bound in the polymerase active site. Modifications in motif B include, but are not limited to, modifications in amino acids located from 13 to 13.5 angstroms from the 3'OH group when nucleotide is bound in the polymerase active site.

Engineered Polymerases

Provided herein are engineered polymerases. The engineered polymerases can be encoded by a nucleic acid set forth herein. The engineered polymerases need not be encoded by any specific nucleic acid exemplified herein. For example, redundancy in the genetic code allows for variations in nucleotide codon sequences that nevertheless encode the same amino acid. Accordingly, engineered polymerases of the present disclosure can be produced from nucleic acid sequences that are different from those set forth herein, for example, being codon optimized for a particular expression system. Codon optimization can be carried out, for example, as set forth in Athey et al. *BMC Bioinformatics* 18:391-401 (2017).

Additionally, provided is an engineered DNA polymerase comprising a variant of SEQ ID NO:1, the variant being at least 80% identical to SEQ ID NO:1 and comprising an amino acid substitution at one or more positions selected from the group consisting of L408, Y409, P410, R484, A/L485, and I486. Also provided is an engineered DNA polymerase comprising a variant of SEQ ID NO:2, the variant being at least 80% identical to SEQ ID NO:2 and comprising an amino acid substitution at one or more positions selected from the group consisting of L408, Y409, P410, R484, A/L485, and I486. Provided is an engineered DNA polymerase comprising a variant of SEQ ID NO:3, the variant being at least 80% identical to SEQ ID NO:3 and comprising an amino acid substitution at one or more positions selected from the group consisting of L408, Y409, P410, R484, A/L485, and I486. Optionally, the variant can be 80, 81, 82, 83, 84, 85, 86, 87, 88, 89, 90, 91, 92, 93, 94, 95, 96, 97, 98, or 99% identical to SEQ ID NO:1, SEQ ID NO:2 or SEQ ID NO:3.

Polymerases of the present disclosure can comprise modifications at amino acid positions L408 and Y409, L408 and P410, Y409 and P410 or L408, Y409 and P410. Optionally, the modifications are selected from the group consisting of L408F, Y409F, Y409H, P410T, P410V. Optionally, the polymerases comprise modifications L408F/Y409F/P410T or L408F/Y409H/P410V.

Alternatively or additionally, the polymerases of the present disclosure can include modifications at amino acid positions R484 and A/L485, R484 and I486, A/L485 and I486, or R484, A/L485 and I486. Optionally, the modifications are selected from the group consisting of R484F, R484I, A/L485H, R484A, R484L, R484S, R484Q, R484T, R484K, R484, A/L485K, A/L485H, A/L485D, A/L485T, A/L485N, A/L485W, A/L485F, I486L, I486V, I486R, I486H, I486F, I486G, or any combination thereof. By way of example, the modifications can be I486V, R484F/I486L, R484I/A/L485K/I486R, A/L485H/I486H, R484A/A/L485D/I486R, R484L, R484S/A/L485T/I486L, R484Q/A/L485T/I486L, R484Q/A/L485T/I486L, R484Q/A/L485T/I486F, R484T/I486V, R484K/A/L485T/I486F, R484L/A/L485N/I486R, A/L485W/I486G, R484L/I486V, or R484S/A/L485F/I486R. As discussed above, the polymerase can include any of the modifications set forth in Table 1.

Preferably, an engineered polymerase of the present disclosure has a function of forming a ternary complex with a primed template nucleic acid and a next correct nucleotide. In particular embodiments, an engineered polymerase will have improved specificity for pairing the next correct nucleotide with the next template base of the primed template nucleic acid, as compared to a control polymerase such as a wild type version of the polymerase or a polymerase that does not contain one or more of the modifications in motif A or motif B of the engineered polymerase. For example, the dissociation constant for binding of the engineered polymerase to the next correct nucleotide can be reduced at least 10%, 50%, 100%, 2 fold, 5 fold, 10 fold, 100 fold or more, as compared to a control polymerase such as a wild type version of the polymerase or a polymerase that does not contain one or more of the modifications in motif A or motif B of the engineered polymerase.

In some embodiments, an engineered polymerase can have a function of catalyzing addition of a next correct nucleotide to the primer of the primer template nucleic acid. In particular embodiments, an engineered polymerase will have increased rate of catalyzing incorporation of a nucleotide into a primer or increased accuracy of nucleotide incorporation, as compared to a control polymerase such as a wild type version of the polymerase or a polymerase that does not contain one or more of the modifications in motif A or motif B of the engineered polymerase. For example, the catalytic rate constant for the engineered polymerase can be increased at least 10%, 50%, 100%, 2 fold, 5 fold, 10 fold, 100 fold or more, as compared to a control polymerase such as a wild type version of the polymerase or a polymerase that does not contain one or more of the modifications in motif A or motif B of the engineered polymerase.

In some embodiments, an engineered polymerase can have low affinity, or no affinity, for binding DNA in the absence of a next correct nucleotide. In particular embodiments, an engineered polymerase can selectivity form ternary complex compared to binary complex. In particular embodiments, an engineered polymerase will have decreased ability to form binary complex with a nucleic acid, as compared to a control polymerase such as a wild type version of the polymerase or a polymerase that does not contain one or more of the modifications in motif A or motif B of the engineered polymerase. For example, the affinity of the engineered polymerase for binding nucleic acid in the absence of a next correct nucleotide can be reduced at least 10%, 50%, 100%, 2 fold, 5 fold, 10 fold, 100 fold or more, as compared to a control polymerase such as a wild type version of the polymerase or a polymerase that does not contain one or more of the modifications in motif A or motif B of the engineered polymerase.

In some embodiments, an engineered polymerase can have little or no function of catalyzing addition of a next correct nucleotide to the primer of a primer template nucleic acid. For example, the catalytic activity of the engineered polymerase can be reduced at least 10%, 50%, 100%, 2 fold, 5 fold, 10 fold, 100 fold or more, as compared to a control polymerase such as a wild type version of the polymerase or a polymerase that does not contain one or more of the modifications in motif A or motif B of the engineered polymerase.

Preferably, an engineered polymerase of the present disclosure substantially lacks exonuclease activity. The engineered polymerases can have a number of advantages over the parental, control, unmodified polymerases. For example, the engineered polymerase can have increased accuracy in pairing nucleotides to template bases as compared to a control polymerase. Optionally, the engineered polymerase has increased stability as compared to a control polymerase. Optionally, the engineered polymerase has improved polymerization kinetic rates as compared to a control polymerase. Optionally, the engineered polymerase has decreased polymerization error rates as compared to a control polymerase. Optionally, the engineered polymerase has an average error rate of less than 0.75 at 100 cycles of a Sequencing By Binding™ (SBB™) process. Optionally, the engineered polymerase has an average error rate of less than 8 at 150 cycles of a SBB™ process. Optionally, the engineered polymerase has an average error rate of between 1 and 5 at 150 cycles of a SBB™ process. Exemplary metrics for determining SBB™ error rates are set forth in the Examples section and elsewhere herein.

Sequence Comparison, Identity, and Homology

The term "identical," in the context of two or more nucleic acid or polypeptide sequences, refers to two or more sequences or subsequences that are the same, when compared and aligned for maximum correspondence, as measured using one of the sequence comparison algorithms described below (or other algorithms available to persons of skill) or by visual inspection. The term "percent identity," in the context of two or more nucleic acid or polypeptide sequences, refers to two or more sequences or subsequences that have a specified percentage of nucleotides or amino acid residues, respectively, that are the same, when compared and aligned for maximum correspondence, as measured using one of the sequence comparison algorithms described below (or other algorithms available to persons of skill) or by visual inspection. By convention, amino acid additions, substitutions, and deletions within an aligned reference sequence are all differences that reduce the percent identity in an equivalent manner. Additional amino acids present at the N- or C-terminus of a polynucleotide compared to the reference have no effect on percent identity scoring for aligned regions. For example, alignment of a 105 amino acid long polypeptide to a reference sequence 100 amino acids long would have a 100% identity score if the reference sequence fully was contained within the longer polynucleotide with no amino acid differences. A single amino acid difference (addition, deletion or substitution) between the two sequences within the 100-amino acid span of the aligned reference sequence would mean the two sequences were 99% identical.

The phrase "substantially identical," in the context of two nucleic acids or polypeptides (e.g., DNAs encoding a polymerase, or the amino acid sequence of a polymerase) refers to two or more sequences or subsequences that have at least about 60%, at least about 80%, at least about 90-95%, at least about 98%, at least about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., at least 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., Current Protocols, a joint venture between Greene Publishing Associates, Inc. and John Wiley & Sons, Inc., supplemented through 2004). The references in this paragraph are incorporated herein.

One example of an algorithm that is suitable for determining percent sequence identity and sequence similarity is the BLAST algorithm, which is described in Altschul et al., *J. Mol. Biol.* 215:403-410 (1990), which is incorporated herein by reference. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915, which is incorporated herein by reference).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993), which is incorporated herein by reference). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Substitution or replacement of one amino acid for another (i.e., so-called "substitution mutations") can be used for modifying functional properties of engineered polymerases. In certain embodiments, a substitution mutation comprises a mutation to a residue having a nonpolar side chain. Amino acids having nonpolar side chains are well known in the art and include, for example: glycine (Gly or G), alanine (Ala or A), valine (Val or V), leucine (Leu or L), isoleucine (Ile or I), methionine (Met or M), phenylalanine (Phe or F), tryptophan (Trp or W), and proline (Pro or P). In certain embodiments, a substitution mutation comprises a mutation to a residue having a polar side chain. Amino acids having polar side chains are well known in the art and include, for example: serine (Ser or S), threonine (Thr or T), cysteine (Cys or C), tyrosine (Tyr or Y), asparagine (Asn or N), and glutamine (Gln or Q). In certain embodiments, a substitution mutation comprises a mutation to a residue having an acidic side chain. Amino acids having acidic side chains are well known in the art and include, for example: aspartate (Asp or D) and glutamate (Glu or E). In certain embodiments, a substitution mutation comprises a mutation to a residue having a basic side chain. Amino acids having basic side chains are well known in the art and include, for example: lysine (Lys or K), arginine (Arg or R), and histidine (His or H).

Useful Recombinant DNA and Protein Expression Techniques

Conventional recombinant DNA cloning techniques can be used to prepare constructs for transformation or transfection ("transformation" hereafter) and expression of nucleic acids encoding engineered polymerases in accordance with the disclosure. Nucleic acid constructs encoding polymerase fragments can be used in combination with synthetic oligonucleotides, standard PCR techniques, and vector ligation to introduce the site-directed mutations needed to produce the polynucleotide sequences disclosed herein. The different constructs can be ligated into a plasmid expression vector, and the plasmid construct introduced into an *E. coli* host using standard transformation techniques. Preferred expression vectors include a T7 promoter sequence upstream of the polymerase-encoding insert, where the T7 promoter is inducible by IPTG or by co-expression of a T7 RNA polymerase. Expressed proteins can include an affinity capture moiety, such as a polyhistidine-tag motif, that facilitates binding of the recombinant protein to an affinity substrate such as a nickel-based resin column that binds to polyhistidine, as part of the purification process.

Embraced by the present description are nucleic acid molecules encoding altered polymerase enzymes. In accordance with various embodiments, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" can also include the complementary sequence to any single stranded sequence given regarding base variations. Nucleic acid molecules encoding the engineered polymerases described herein may also be included in a suitable expression vector to express the polymerase proteins encoded therefrom in a suitable host. Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a recombinant protein. Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and AUG start codon. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences well known in the art.

Covered nucleic acid molecules may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Recombinant polymerase proteins can be, and indeed several engineered variants were, further purified and concentrated using conventional laboratory techniques that will be familiar to those having an ordinary level of skill in the art. Purified polymerase samples were stored at −80° C. until being used.

Accordingly, the present disclosure provides a nucleic acid construct comprising one or more of the provided nucleic acids encoding the engineered polymerases set forth herein. The nucleic acid construct is optionally a plasmid or vector. The nucleic acid construct can include elements that allow replication of the construct, biological selection for the construct and/or expression of the one or more proteins encoded by the construct. Suitable vector backbones include, for example, those routinely used in the art such as plasmids, artificial chromosomes, BACs, or PACs. Numerous vectors and expression systems are commercially available from such corporations as MilliporeSigma (St. Louis, Mo.), Clonetech (a subsidiary of Takara, Mountain View, Calif.), Agilent (La Jolla, Calif.), and ThermoFisher (Waltham, Mass.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

The present disclosure also provides recombinant organisms that include a nucleic acid construct that encodes one or more of the engineered polymerases set forth herein. A recombinant organism of the present disclosure can be configured to express one or more polymerase having a sequence set forth herein. Furthermore, the present disclosure provides a recombinant organism that comprises a polymerase having a sequence set forth herein.

Further, a cultured cell is provided that is transformed or transfected ("transformed" hereafter) with a vector comprising a nucleic acid construct described herein. In this regard, a cell is successfully transformed with a vector when the transcription machinery of the intact cell has access to the nucleic acid template for the production of mRNA. Protocols to facilitate transformation of vectors into cells are well known in the art. Also provided herein are the progeny of a cultured cell that was stably transformed with the vector as described above. Such progeny will contain copies of the vector without having undergone the transformation protocol and are capable of transcribing the nucleic acids contained in vector under the control of an expression control sequence. Techniques utilizing cultured cells transformed with expression vectors to produce quantities of polypeptides are well known in the art.

Polymerases Suitable for Engineering

Polymerases suitable as backbones for engineering as described herein include, but are not limited to, archaeal, bacterial, and eukaryotic polymerases having the known and conserved regions referred to as motif A and motif B. Motif A is a conserved region among polymerases involved in nucleotide binding and substrate specificity. Optionally, motif A refers specifically to amino acids 408-410, or to the motif that includes amino acids 408-410, of the polymerases having sequences listed in SEQ ID Nos: 1, 2 or 3. Motif B refers to the conserved region among polymerases involved in nucleotide binding. Optionally, motif B refers specifically to amino acids 484-486, or to the motif that includes amino acids 484-486, of the polymerases having sequences listed in SEQ ID Nos: 1, 2 or 3. As discussed above, Motif A and Motif B are known and used to refer to regions of sequence homology in the nucleotide binding sites of B family and other polymerases. Thus, the polymerase is optionally a B-type family DNA polymerase. Useful B-type Family DNA polymerases include any DNA polymerase that is classified as a member of the Family B DNA polymerases, where the Family B classification is based on structural similarity to *E. coli* DNA polymerase II. B-type family polymerases include bacterial and bacteriophage polymerases including *E. coli* DNA polymerase II; PRD 1 DNA polymerase; phi29 DNA polymerase; M2 DNA polymerase; and T4 DNA polymerase. B-type family polymerases also include archaeal DNA polymerases such as *Thermococcus litoralis* DNA polymerase (Vent); *Pyrococcus furiosus* DNA polymerase; *Sulfolobus solfataricus* DNA polymerase; *Thermococcus gorgonarius* DNA polymerase (TGO polymerase); *Thermococcus* species TY (65); *Pyrococcus* species strain KODI (KOD polymerase); *Sulfolobus acidocaldarius* DNA polymerase; *Thermococcus* species 9° N-7 (Therminator™); *Thermococcus* species 9° N; *Pyrodictium occultum* DNA polymerase; *Methanococcus voltae* DNA polymerase; and *Desulfurococcus* strain TOK (D. Tok Pol). Eukaryotic B-type family DNA polymerases include, but are not limited to, DNA polymerase alpha; Human DNA polymerase (alpha); *S. cerevisiae* DNA polymerase (alpha); *S. pombe* DNA polymerase I (alpha); *Drosophila melanogaster* DNA polymerase (alpha); *Trypanosoma brucei* DNA polymerase (alpha); DNA polymerase delta; Human DNA polymerase (delta); Bovine DNA polymerase (delta); *S. cerevisiae* DNA polymerase III (delta); *S. pombe* DNA polymerase III (delta); and *Plasmodiun falciparum* DNA polymerase (delta).

Polymerases other than the ones described herein with functionally equivalent or homologous "motif A" and "motif B" regions can be identified on the basis of amino acid sequence alignment and/or molecular modelling. Sequence alignments may be compiled using any of the standard alignment tools known in the art, such as for example BLAST and the like. Other polymerases that can be engineered include, for example, those that are members of families identified as A, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* Pol I, and *Bacillus stearothermophilus* Pol I. Family C includes, for example, the *E. coli* DNA Polymerase III alpha subunit. Family D includes, for example, polymerases derived from the Euryarchaeota subdomain of Archaea. DNA Polymerases in Family X include, for example, eukaryotic polymerases Pol β, pot σ, Pol λ, and Pol μ, and *S. cerevisiae* Pol4. DNA Polymerases in Family Y include, for example, Pol η, Pol ι, Pol κ, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Motif A is present in RNA polymerases and can be modified at positions set forth herein regarding to DNA polymerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

Useful Polymerase Labeling and Processing Techniques

Depending on the application, engineered polymerases according to the disclosure may be either labeled with a detectable label, or unlabeled. Unlabeled polymerases may be used in label-free systems, or alternatively can be used in conjunction with detectably labeled nucleotides and/or template nucleic acids. Detectably labeled polymerases can be used in combination with unlabeled nucleotides, or unlabeled primer or template nucleic acids for cognate nucleotide identification. Of course, the engineered polymerases may simply be used for synthesizing DNA strands in template-dependent DNA synthesis reactions.

Engineered polymerases can be covalently modified, post-purification, to contain a fluorescent moiety. For example, a fluorescent moiety can be joined to the free sulfhydryl of a Cys residue located toward the N-terminal ends of a protein. For example, a Cy-5 fluorescent label chemically activated as a maleimide ester can be joined to the free thiol functional group of the N-terminal region Cys residue using standard protein labeling techniques. Further examples of useful fluorescent labels are set forth in sections below. While use of labeled engineered polymerases is exemplified herein using a fluorescent label, many other types of labels also may be used. Moreover, other attachment chemistries can be used as well. For example, an engineered polymerase can be expressed from a gene fusion construct in which coding sequence for a protein label, such as green fluorescent protein, phycobiliprotein or color shifted variants thereof, is fused to coding sequence for the polymerase.

Alternative labels may be used for labeling engineered polymerases in accordance with the disclosure. Labels attached to the polymerases can be detectable by changes in any of: refractive index, charge detection, Raman scattering detection, ellipsometry detection, pH detection, size detection, mass detection, surface plasmon resonance, guided mode resonance, nanopore optical interferometry, whispering gallery mode resonance, nanoparticle scattering, photonic crystal, quartz crystal microbalance, bio-layer interferometry, vibrational detection, pressure detection and other label free detection schemes that detect the added mass or refractive index due to polymerase binding in a closed-complex with a template nucleic acid, and the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like. Further examples of useful labels are set forth in sections below.

A polymerase, nucleotide or other molecule set forth herein can be labeled with a fluorophore and/or quencher. Exemplary fluorophores include, but are not limited to, fluorescent nanocrystals; quantum dots; green fluorescent protein and color shifted mutants thereof, phycobiliproteins such as phycocyanin and phycoerythrin, d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorophores include, but are not limited to, MDCC (7-diethylamino-3-[([(2-maleimidyl)ethyl]amino)carbonyl] coumarin), TET, HEX, Cy3, TMR, ROX, Texas Red, Cy5, LC red 705 and LC red 640. Fluorophores and methods for their use including attachment to polymerases and other molecules are described in The Molecular Probes® Handbook (Life Technologies, Carlsbad Calif.) and Fluorophores Guide (Promega, Madison, Wis.), which are incorporated herein by reference. Exemplary quenchers include, but are not limited to, ZEN, IBFQ, BHQ-1, BHQ-2, DDQ-I, DDQ-11, Dabcyl, Qx1 quencher, Iowa Black RQ, and IRDye QC-1.

Polymerases in accordance with the disclosure can be subjected to further post-purification processing to enhance functional properties or modify structure. This can involve chemical modification and/or enzymatic processing. Optionally, a portion of the engineered polymerase is cleaved from the remainder of the polypeptide, and removed.

During performance of a Sequencing By Binding™ procedure, the engineered polymerase can be used to identify cognate nucleotide, for example, during an examination step. Optionally the engineered polymerase can also be used for incorporating the same or a different type of nucleotide into a primer during an extension step. For example, in some embodiments it is preferable to remove engineered polymerase and nucleotide following an examination step, and then to replace that first polymerase and nucleotide with the same or different nucleotide and a different polymerase. Optionally, the replaced nucleotide can be a reversible terminator nucleotide (e.g., an unlabeled reversible terminator nucleotide). In some embodiments, an engineered polymerase of the present disclosure is used for an extension step, but not for an examination step of a Sequencing By Binding™ procedure.

Allele-Specific Capture Using Engineered Polymerases

Engineered polymerases in accordance with the disclosure can be used to perform allele-specific capture of target nucleic acids, for example as described in commonly owned U.S. Pat. App. Pub. No. 2017/0022553 A1, which is incorporated by reference herein. More particularly, engineered polymerases can be used for selecting or capturing nucleic acids having target alleles of interest. For example, a stabilized ternary complex can be formed between a polymerase, target allele and cognate nucleotide for the allele. Polymerase specificity allows a target allele to be separated from other nucleic acids, including for example, other alleles that differ from the target allele by a single nucleotide.

Provided is a method for separating a target allele from a mixture of nucleic acids includes the step of (a) providing a mixture of nucleic acids in fluidic contact with a stabilized ternary complex that is attached to a solid support. The stabilized ternary complex can include an engineered polymerase, a primed nucleic acid template, and a next correct nucleotide. The template can include a target allele, where the next correct nucleotide is a cognate nucleotide for the target allele. The stabilized ternary complex can be attached to the solid support via a linkage between the polymerase and the solid support, or via a linkage between the next correct nucleotide and the solid support. The method can also include the step of (b) separating the solid support from the mixture of nucleic acids, thereby separating the target allele from the mixture of nucleic acids.

A method for separating a plurality of target alleles from a mixture of nucleic acids is provided. The method can include the step of (a) providing a mixture of nucleic acids in fluidic contact with a plurality of stabilized ternary complexes that are solid support-attached. The stabilized ternary complexes can each include an engineered polymerase, a primed nucleic acid template, and a next correct nucleotide. The template can include a target allele, and the next correct nucleotide can be a cognate nucleotide for the target allele. Each of the stabilized ternary complexes can be attached to the solid support via a linkage between the polymerase and the solid support, or via a linkage between the next correct nucleotide and the solid support. The method can also include the step of (b) separating the solid support from the mixture of nucleic acids, thereby separating the target alleles from the mixture of nucleic acids.

Provided is a method for separating a first allele of a locus from a second allele at the locus that includes the step of (a) providing a mixture including the second allele in fluidic contact with a stabilized ternary complex that is attached to a solid support. The stabilized ternary complex can include an engineered polymerase, a primer hybridized to a nucleic acid template, and a next correct nucleotide. The template can include the first allele. The next correct nucleotide can be a cognate nucleotide for the first allele, or the 3'-end of the primer can include a cognate nucleotide for the first allele. The stabilized ternary complex can be attached to the solid support via a linkage between the polymerase and the solid support, or via a linkage between the next correct nucleotide and the solid support. The method can also include the step of (b) separating the solid support from the mixture of nucleic acids, thereby separating the first allele from the second allele.

A method for separating first alleles at a plurality of loci from second alleles at the plurality of loci, respectively, can include the step of (a) providing a mixture of the second alleles at the plurality of loci, respectively, in fluidic contact with a plurality of stabilized ternary complexes that are solid support-attached. The stabilized ternary complexes can each include an engineered polymerase, a primed nucleic acid template, and a next correct nucleotide. The template can include a first allele, where the next correct nucleotide is a cognate nucleotide for the first allele, or the 3'-end of the primer can include a cognate nucleotide for the first allele. Each of the stabilized ternary complexes can be attached to the solid support via a linkage between the polymerase and the solid support, or via a linkage between the next correct nucleotide and the solid support. The method can also include the step of (b) separating the solid support from the mixture of nucleic acids, thereby separating the first alleles from the second alleles at the plurality of loci.

Genotyping Using Engineered Polymerases

Engineered polymerases in accordance with the disclosure can be used to perform genotyping by polymerase binding, for example as described in commonly owned U.S. Publication No. 2017/0022553 A1, which is incorporated by reference herein. For example, a ternary complex can be formed between an engineered polymerase, a primed template encoding a target single nucleotide polymorphism (SNP) allele and a cognate nucleotide for the SNP allele. Detection of the ternary complex can provide selective detection of the SNP allele, compared to a non-target SNP allele at the same locus, because the cognate nucleotide is selective for the target SNP when forming a ternary complex with the polymerase.

Provided is a method for identifying target alleles in a mixture of nucleic acids. The method can include the steps of (a) providing an array of features, where different locus-specific primers are attached at different features of the array and (b) contacting the array with a plurality of nucleic acid templates, engineered polymerases and nucleotides to form a plurality of stabilized ternary complexes at a plurality of the features. The stabilized ternary complexes can each include an engineered polymerase, a template nucleic acid including a target allele of a locus, a locus-specific primer of the array hybridized to the locus, and a next correct nucleotide that is a cognate to the target allele. The method can also include the step of (c) detecting stabilized ternary complexes at the features, thereby identifying the target alleles.

A method for identifying target alleles in a mixture of nucleic acids is also provided. The method can include the steps of (a) providing an array of features, where different allele-specific primers are attached at different features of the array and (b) contacting the array with a plurality of nucleic acid templates, engineered polymerases and nucleotides to form a plurality of stabilized ternary complexes at a plurality of the features. The stabilized ternary complexes can each include an engineered polymerase, a template nucleic acid including a target allele of a locus, an allele-specific primer of the array hybridized to the locus, and a next correct nucleotide having a cognate in the locus. The 3'-end of the allele-specific primer can include a cognate nucleotide for the target allele. The method can also include the step of (c) detecting stabilized ternary complexes at the features, thereby identifying the target alleles.

Also provided is a method for identifying target alleles in a mixture of nucleic acids that includes the steps of (a) providing an array of features, where different locus-specific primers are attached at a first subset of the features of the array, and wherein different allele-specific primers are attached at a second subset of the features of the array; and (b) contacting the array with a plurality of nucleic acid templates, engineered polymerases and nucleotides to form a plurality of stabilized ternary complexes at a plurality of the features. The stabilized ternary complexes at the first subset of features can each include an engineered polymerase, a template nucleic acid including a target allele of a locus, a locus-specific primer of the array hybridized to the locus, and a next correct nucleotide that is a cognate to the target allele. The stabilized ternary complexes at the second subset of features can each include an engineered polymerase, a template nucleic acid including a target allele of a locus, an allele-specific primer of the array hybridized to the locus, and a next correct nucleotide having a cognate in the locus. The 3'-end of the allele-specific primer can include a cognate nucleotide for the target allele. The method can also include the step of (c) detecting stabilized ternary complexes at the features, thereby identifying the target alleles.

A method for identifying target alleles in a mixture of nucleic acids can include the steps of (a) providing an array of features, where different template nucleic acids are attached at different features of the array, and (b) contacting the array with a plurality of primers, engineered polymerases and nucleotides to form a plurality of stabilized ternary complexes at a plurality of the features. The stabilized ternary complexes at the features can each include an engineered polymerase, a template nucleic acid attached to a feature of the array and including a target allele of a locus, a primer hybridized to the locus, and a next correct nucleotide having a cognate in the locus, where either: (i) the primer is an allele-specific primer including a 3' nucleotide that is a cognate nucleotide for the target allele, or (ii) the primer is a locus-specific primer and the next correct nucleotide hybridizes to the target allele. The method can also include the step of (c) detecting stabilized ternary complexes at the features, thereby identifying the target alleles.

A method for identifying target alleles in a mixture of nucleic acids can include the steps of (a) providing an array of features, where engineered polymerases are attached at features of the array, and (b) contacting the array with a plurality of primers, template nucleic acids and nucleotides to form a plurality of stabilized ternary complexes at a plurality of the features. The stabilized ternary complexes at the features can each include an engineered polymerase that is attached at a feature of the array, a template nucleic acid including a target allele of a locus, a primer hybridized to the locus, and a next correct nucleotide having a cognate in the locus, where either: (i) the primer is an allele-specific primer including a 3' nucleotide that is a cognate nucleotide for the target allele, or (ii) the primer is a locus-specific primer and the next correct nucleotide hybridizes to the target allele. The method can also include the step of (c) detecting stabilized ternary complexes at the features, thereby identifying the target alleles.

Sequencing by Binding™ Methods Using Engineered Polymerases

Provided herein are polymerase-based nucleic acid sequencing methods that utilize an engineered polymerase. Use of the engineered polymerases for sequencing will be exemplified in the context of Sequencing By Binding™ reactions. However, the engineered polymerases can be used to replace polymerases used in other sequencing techniques such as cyclic reversible terminator sequencing (see, for example, U.S. Pat. No. 7,057,026, US pat. App. Pub. Nos. 2007/0166705 A1, 2006/0188901 A1, 2006/0240439 A1, 2006/0281109 A1, or 2005/0100900 A1, the disclosures of which are incorporated herein by reference, or sequencing by synthesis (SBS) platforms commercially available from Illumina, Inc., San Diego Calif.); SBS techniques that use proton detection (see, US Pat. App. Pub. Nos. 2009/0026082 A1; 2009/0127589 A1; 2010/0137143 A1; or 2010/0282617 A1, each of which is incorporated herein by reference, or Ion Torrent platforms commercially available from Thermo Fisher (Waltham, Mass.)); SBS techniques that utilize single molecule detection (see, for example, Levene et al. *Science* 299, 682-686 (2003); Lundquist et al. Opt. Lett. 33, 1026-1028 (2008); Korlach et al. Proc. Natl. Acad. Sci. USA 105, 1176-1181 (2008)); pyrosequencing (see, for example, Ronaghi, et al., *Anal. Biochem.* 242 (1), 84-9 (1996); Ronaghi, *Genome Res.* 11 (1), 3-11 (2001); Ronaghi et al. *Science* 281 (5375), 363 (1998); or U.S. Pat. Nos. 6,210,891; 6,258,568 or 6,274,320, each of which is incorporated herein by reference); or polymerase-facilitated nanopore sequencing (see, for example, techniques being commercialized by Oxford Nanopore (Oxford, UK) or Genia (a subsidiary of Roche, Basel, Switzerland)

Continuing with the example of Sequencing By Binding™ reactions, polymerase can bind to a primed template nucleic acid to form a binary complex, also referred to herein as the pre-insertion conformation. In such embodiments, an incoming nucleotide can be bound and the polymerase can form a pre-chemistry conformation comprising the polymerase, primed template nucleic acid and nucleotide; wherein the bound nucleotide has not been incorporated. This step may be followed by an incorporation process wherein a $Mg^{2+}$- or $Mn^{2+}$-catalyzed chemical incorporation of the next correct nucleotide, wherein nucleophilic displacement of a pyrophosphate (PPi) by the 3'-hydroxyl of the primer results in phosphodiester bond formation. The polymerase can then release PPi following nucleotide incorporation, and translocation of the polymerase can step to the next template base for detection in the next cycle of the reaction. Formation of the binary complex is optional. In some embodiments, all components sufficient to form a ternary complex are delivered in a way that a ternary complex can be formed without necessarily forming a binary complex. Certain details of the Sequencing By Binding™ procedure can be found in commonly owned U.S. Publication Nos. US 2017/0022553 A1 or 2018/0044727 A1 or U.S. Pat. No. 9,951,385, each of, which is incorporated by reference herein.

While a ternary complex including a primed template nucleic acid molecule having a primer with a free 3'-hydroxyl can form in the absence of a divalent catalytic metal ion (e.g., $Mg^{2+}$), chemical addition of nucleotide can proceed in the presence of the divalent metal ions. Low or deficient levels of catalytic metal ions, such as $Mg^{2+}$ tend to lead to non-covalent (physical) sequestration of the next correct nucleotide in a ternary complex. This ternary complex may be referred to as a stabilized or trapped ternary complex. Other methods disclosed herein also can be used to produce a stabilized ternary complex. In any reaction step described above, the polymerase configuration and/or interaction with a nucleic acid may be monitored during an examination step to identify the next correct base in the nucleic acid sequence. Before or after incorporation, reaction conditions can be changed to disengage the polymerase from the primed template nucleic acid, and changed again to remove from the local environment any reagents that inhibit polymerase binding.

Generally speaking, a Sequencing By Binding™ procedure can include an "examination" step that detects ternary complex, and optionally a subsequent "incorporation" step that adds one or more complementary nucleotides to the 3'-end of the primer component of the primed template nucleic acid. Identity of the next correct nucleotide in the ternary complex can be determined either without, or before chemical linkage of that nucleotide to the 3'-end of the primer through a covalent bond. The examination step can involve providing a primed template nucleic acid to be used in the procedure, and contacting the primed template nucleic acid with a polymerase enzyme (e.g., a DNA polymerase) composition and one or more test nucleotides being investigated as the possible next correct nucleotide. Further, there is a step that involves monitoring or measuring the interaction between the polymerase and the primed template nucleic acid in the presence of the test nucleotides.

Optionally, monitoring of the interaction can take place when the primer of the primed template nucleic acid molecule includes a blocking group that precludes enzymatic incorporation of an incoming nucleotide into the primer. The interaction additionally or alternatively can take place in the presence of stabilizers (e.g., non-catalytic metal ions that inhibit incorporation), whereby the polymerase-nucleic acid interaction is stabilized in the presence of the next correct nucleotide (i.e., stabilizers that stabilize the ternary complex). Again, the examination step identifies or determines the identity of the next correct nucleotide without requiring incorporation of that nucleotide. Stated differently, identity of the next correct nucleotide can be established without chemical incorporation of the nucleotide into the primer, whether or not the 3'-end of the primer is blocked.

Whereas methods involving a single template nucleic acid molecule may be described for convenience, these methods are exemplary. The sequencing methods provided herein readily encompass a plurality of template nucleic acids, wherein the plurality of nucleic acids may be clonally amplified copies of a single nucleic acid, or disparate nucleic acids, including combinations, such as populations of disparate nucleic acids that are clonally amplified.

Examination Steps

An examination step in a Sequencing By Binding™ procedure can include the following sub-steps: (1) contacting a primed template nucleic acid molecule with a reaction mixture that includes at least one polymerase and one nucleotide; (2) detecting the interaction of the polymerase with the primed template nucleic acid molecule in the presence of the nucleotide and without chemical incorporation of any nucleotide into the primed template nucleic acid; and (3) determining from the detected interaction the identity of the next base in the template nucleic acid. In particular embodiments, a polymerase can be distinguished from others used in the procedure by virtue of including a detectable label, or by timing of delivery to a primed template nucleic acid molecule. Alternatively or additionally, a nucleotide can be distinguished from others used in the procedure by virtue of including a detectable label, or by timing of delivery to a primed template nucleic acid molecule.

An examination step optionally includes: (1) serially contacting a primed template nucleic acid with a plurality of distinguishably labeled polymerase-nucleotide combinations under conditions that discriminate between formation of ternary complexes and binary complexes; (2) detecting any ternary complexes that formed as a result of the serial contacting steps by detecting one or more of the distinguishably labeled polymerases from the combinations used in the different contacting steps; and (3) identifying the next correct nucleotide for the primed template nucleic acid as the nucleotide component of the distinguishably labeled polymerase-nucleotide combination that formed the ternary complex. While a ternary complex may be stabilized by non-catalytic cations that inhibit nucleotide incorporation or polymerization, primers blocked at their 3'-ends provide alternative stabilization approaches. A trivalent lanthanide cation or other stabilizing agent (e.g., a divalent metal ion that inhibits incorporation, or a trivalent metal ion that inhibits incorporation) may be used to inhibit dissociation of the complex (e.g., to "lock" the ternary complex in place). Optionally, a detectably labeled polymerase is delivered to an immobilized primed template nucleic acid molecule in a flow cell in combination with a single nucleotide to assess whether or not the nucleotide is the next correct nucleotide to be incorporated.

The primer of a primed template nucleic acid optionally can be either an extendible primer, or a primer blocked from extension at its 3'-end (e.g., by the presence of a reversible terminator moiety). The primed template nucleic acid, the polymerase and the test nucleotide are capable of forming a ternary complex when the base of the test nucleotide is complementary to the next base of the primed template nucleic acid molecule. In some embodiments, the primed template nucleic acid and the polymerase are capable of forming a binary complex when the base of the test nucleotide is not complementary to the next base of the primed template nucleic acid molecule. Optionally, the contacting occurs under conditions that favor formation of the ternary complex over formation of the binary complex. Optionally, the conditions that favor or stabilize the ternary complex are provided by one or both of: (1) the presence of a reversible terminator moiety on the 3' nucleotide of the primer of the primed template nucleic acid molecule; or (2) the presence of a non-catalytic ion that inhibits nucleotide incorporation or polymerization. Optionally, the conditions that disfavor or destabilize binary complexes are provided by the presence of one or more monovalent cations and/or glutamate anions in the reaction mixture during the examination step. Alternatively or in addition to using these conditions, an engineered polymerase having reduced catalytic activity or reduced propensity for binary complex formation can be used. The determining or identifying step can include identifying the base of the nucleotide that is complementary to the next base of the primed template nucleic acid. This can be accomplished by detecting the ternary complex (e.g., via a label attached to the polymerase and/or a label attached to the nucleotide), and deducing identity of the cognate nucleotide from that identification.

A polymerase inhibitor optionally may be included in the examination step to trap the polymerase on the nucleic acid upon binding the next correct nucleotide. Optionally, the polymerase inhibitor is a pyrophosphate analog. Optionally, the polymerase inhibitor is an allosteric inhibitor. Optionally, the polymerase inhibitor is a DNA or an RNA aptamer. Optionally, the polymerase inhibitor competes with a catalytic ion-binding site in the polymerase. Optionally, the polymerase inhibitor is a reverse transcriptase inhibitor. The polymerase inhibitor may be an HIV-1 reverse transcriptase inhibitor or an HIV-2 reverse transcriptase inhibitor. The HIV-1 reverse transcriptase inhibitor may be a (4/6-halogen/MeO/EtO-substituted benzo[d]thiazol-2-yl)thiazolidin-4-one.

The examination step can be controlled so that nucleotide incorporation is attenuated or precluded during the step. This being the case, a separate incorporation step (discussed elsewhere herein in greater detail) may be performed. The separate incorporation step may be accomplished without the need for monitoring, as the base has already been identified during the examination step. However if desired, subsequent incorporation can be detected, for example, by incorporating nucleotides having exogenous labels. Detection at both binding and incorporation steps can provide for error checking and increased sequencing accuracy. A reversibly terminated nucleotide (whether labeled or not) may be used in the incorporation step to prevent the addition of more than one nucleotide during a single cycle.

The Sequencing By Binding™ method allows for controlled determination of a template nucleic acid base without the need for labeled nucleotides, as the interaction between the polymerase and template nucleic acid can be monitored without a label on the nucleotide. Template nucleic acid molecules may be sequenced under examination conditions that do not require attachment of template nucleic acid or polymerase to a solid support. However, primed template nucleic acids to be sequenced can be attached to a solid support, such as an interior surface of a flow cell. Accordingly, a polymerase having a sequence set forth herein can form a stabilized ternary complex on a solid support via binding to a primed template nucleic acid that is attached to the solid support.

Alternatively or in addition to attaching primed template nucleic acids to a solid support, one or more polymerase molecules can be attached to the solid support. Attachment of polymerase to a solid support can provide an advantage in localizing the polymerase for a subsequent detection step. This can be useful for example, when screening polymerase variants for ability to form a stabilized ternary complex with a primed template nucleic acid and nucleotide that are delivered via solution phase. Alternatively, attachment of the polymerase can be useful for localizing the polymerase at a feature where a particular nucleic acid resides. The polymerase can be attached to a solid support for uses other than sequencing, including, but not limited to allele-capture or genotyping as set forth herein or as set forth in U.S. Pat. App. Pub. No. 2017/0022553 A1 or U.S. Pat. No. 9,932,631, each of which is incorporated herein by reference.

Optionally, the provided methods further include a wash step. The wash step can occur before or after any other step in the method. Optionally, the wash step is performed after each of the serial contacting steps, wherein the primed template nucleic acid molecule is contacted with one of the distinguishably labeled polymerase-nucleotide combinations. Optionally, the wash step is performed prior to the monitoring step and/or prior to the determining or identifying step. Optionally, the wash step occurs under conditions that stabilize the ternary complex. for example, the conditions can result from the presence of a reversible terminator moiety on the 3' nucleotide of the primer of the primed template nucleic acid molecule, presence of a stabilizing agent such as a non-catalytic metal ion. Optionally, the wash buffer includes nucleotides of the same type as used in the previous contacting steps. Including the nucleotides from previous contacting steps can provide the advantage of stabilizing previously formed ternary complexes from unwanted disassociation. Polymerases of the type present in a previous contacting step can optionally be included in a wash step. In some embodiments nucleotides, whether the same as or different from those used in a previous contacting step are not delivered via a wash step. In some embodiments polymerases, whether the same as or different from those used in a previous contacting step are not delivered via a wash step. Optionally, a ternary complex has a half-life and a wash step is performed for a duration shorter than the half-life of the ternary complex. Similar wash techniques can be used in other methods that use an engineered polymerase including, but not limited to allele capture or genotyping methods such as those set forth herein or in U.S. Pat. App. Pub. No. 2017/0022553 A1 or U.S. Pat. No. 9,932,631, each of which is incorporated herein by reference.

Optionally, the examination conditions accentuate the difference in affinity for polymerase to primed template nucleic acids in the presence of different nucleotides, for example by destabilizing binary complexes. Optionally, the examination conditions cause differential affinity of the polymerase for the primed template nucleic acid in the presence of different nucleotides. By way of example, the examination conditions that cause differential affinity of the polymerase for the primed template nucleic acid in the presence of different nucleotides include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate anions. Optionally, the source of glutamate ions can be potassium glutamate. Exemplary concentrations of potassium glutamate that can be used to alter polymerase affinity of the primed template nucleic acid extend from 10 mM to 1.6 M of potassium glutamate, or any amount in between 10 mM and 1.6 M. As indicated above, high salt refers to a concentration of salt from 50 to 1,500 mM salt.

Optionally, examination involves detecting polymerase interaction with a template nucleic acid where the interaction of one or more polymerase compositions can be distinguished. Optionally, examination is performed after a wash step, wherein the wash step removes any non-bound reagents (e.g., unbound polymerases and/or nucleotides) from the region of observation. This may occur at the end of a series of steps involving contacting of a primed template nucleic acid molecule with a plurality of distinguishable polymerase-nucleotide combinations. Optionally, examination is performed during a wash step, such that the dissociation kinetics of the polymerase-nucleic acid or polymerase-nucleic acid-nucleotide complexes may be monitored and used to determine the identity of the next base. Optionally, examination is performed during the course of addition of the examination reaction mixture (or first reaction mixture), such that the association kinetics of the polymerase to the nucleic acid may be monitored and used to determine the identity of the next base on the nucleic acid. Optionally, examination is performed under equilibrium conditions where the affinities measured are equilibrium affinities.

Optionally, ternary complex formation is facilitated by the use of a flow cell or chamber, multiwell plate, etc. Flowing liquid reagents through the flow cell, which contains an interior solid support surface (e.g., a planar surface), conveniently permits reagent exchange or replacement. One or more primed nucleic acid can be immobilized to a surface in a flow cell. Liquid reagents (e.g., polymerase, nucleotide or other components of the "reaction mixtures" discussed herein) can be delivered to the surface via an entry port. Liquid reagents can be removed from the flow cell by exiting through an exit port.

Monitoring formation, presence or dissociation of a ternary complex may be accomplished in many different ways. For example, monitoring can include measuring association kinetics for the interaction between the primed template nucleic acid, the polymerase, and any one of the four nucleotide molecules. Monitoring the interaction of the polymerase with the primed template nucleic acid molecule in the presence of a nucleotide molecule can include measuring binding (e.g. determining an equilibrium binding constant) between the polymerase and primed template nucleic acid molecule. Thus, for example, the monitoring can include measuring binding of the polymerase to the primed template nucleic acid in the presence of one or more nucleotides. Monitoring interaction of ternary complex components includes, for example, measuring dissociation kinetics of the polymerase from the primed template nucleic acid in the presence of particular nucleotide types, or measuring association kinetics of the polymerase for the primed template nucleic acid in the presence of particular nucleotide types. Monitoring of these interactions can be carried out without chemical incorporation of nucleotides into the primer of the primed template nucleic acid molecule. Optionally, the measured dissociation or association kinetics are different depending on the identity of the nucleotide molecule. Optionally, the polymerase has a different affinity for each of the four types of nucleotide molecules. Optionally, the polymerase has a different dissociation constant for each of the four types of nucleotide molecules in each type of ternary complex. Techniques for determining association, equilibrium and dissociation kinetics are known and can be readily determined by one skilled in the art. See, for example, Markiewicz et al., *Nucleic Acids Research* 40(16): 7975-84 (2012); Xia et al., *J. Am. Chem. Soc.* 135(1):193-202 (2013); Brown et al., *J. Nucleic Acids*, Article ID 871939, 11 pages (2010); Washington, et al., *Mol. Cell. Biol.* 24(2):936-43 (2004); Walsh and Beuning, *J. Nucleic Acids*, Article ID 530963, 17 pages (2012); and Roettger, et al., *Biochemistry* 47(37):9718-9727 (2008), which are incorporated by reference herein. It will be understood that a monitoring technique can accumulate and combine signals for a single timepoint acquisition or, alternatively, signals can be acquired in a time resolved manner as is typical of a time-based acquisition. It is also possible to acquire a series of timepoints to obtain a time-based acquisition.

In the sequencing methods provided herein, either a chemical block on the 3' nucleotide of the primer of the primed template nucleic acid molecule, the absence of a catalytic metal ion in the reaction mixture, or the absence of a catalytic metal ion in the active site of the polymerase can prevent the chemical incorporation of the nucleotide into the primer of the primed template nucleic acid. Optionally, the chelation of a catalytic metal ion in the reaction mixtures of the contacting step prevents the chemical incorporation of the nucleotide into the primer of the primed template nucleic acid. Optionally, a non-catalytic metal ion acts as a stabilizer for the ternary complex in the presence of the next correct nucleotide. Optionally, the substitution of a catalytic metal ion in the reaction mixtures of the contacting step with a non-catalytic metal ion prevents the chemical incorporation of the nucleotide molecule to the primed template nucleic acid.

Incorporation Steps

Optionally, incorporation proceeds after the cognate nucleotide has been identified in an examination procedure using a first polymerase. Incorporation optionally may employ a polymerase different from the one used in the examination step, e.g., a second polymerase. Optionally, incorporation may involve incorporation of a non-natural nucleotide analog. For example, the non-natural nucleotide analog can be a reversible terminator nucleotide having a base that is a cognate of the next template base. The incorporated base need not include an exogenous label; however, an exogenous label can be present if desired.

Optionally, an incorporation step involves covalently incorporating one or more nucleotides at the 3'-end of a primer hybridized to a template nucleic acid. In a preferred embodiment, only a single nucleotide is incorporated at the 3'-end of the primer. Optionally, multiple nucleotides of the same kind are incorporated at the 3'-end of the primer. Optionally, multiple nucleotides of different kinds are incorporated at the 3'-end of the primer. Incorporated nucleotides alternatively can be unlabeled nucleotides, reversible terminator nucleotides, or detectably labeled nucleotide analogs.

An incorporation reaction may be facilitated by an incorporation reaction mixture. Optionally, the incorporation reaction mixture has a different composition of nucleotides than the examination reaction. For example, the examination reaction can include one type of nucleotide and the incorporation reaction can include another type of nucleotide. In this example, the two types of nucleotides can have the same base moiety while differing at another moiety, for example, differing with respect to the presence or absence of a blocking group on the sugar moiety. An incorporation reaction can be carried out by the same polymerase that was used for examination, by a polymerase of the same type as the polymerase used for examination, or by a polymerase that differs from the polymerase used for examination. An incorporation step can be carried out in the presence of one or more nucleotides that complement at least 1, 2, 3 or 4 different bases expected to be present in a template nucleic acid that is being sequenced. For example, an examination step can include one type of nucleotide and an incorporation reaction comprises four types of nucleotides, or vice versa. In yet another example, an examination step uses four different reagent deliveries, each containing one of four types of nucleotides, such that the four types of nucleotides are sequentially present, whereas the incorporation reaction can include the four types of nucleotides in a simultaneous mixture. As a further example, a first examination reaction can introduce a first type of nucleotide, a second examination reaction can introduce a second type of nucleotide along with the first type of nucleotide, a third examination reaction can introduce a third type of nucleotide along with the first and second types of nucleotides, a fourth examination reaction can introduce a fourth type of nucleotide along with the first, second and third types of nucleotides, and the incorporation reaction can include the first, second, third and fourth types of nucleotides in a simultaneous mixture. Optionally, an examination reaction mixture is altered or replaced by an incorporation reaction mixture. Optionally, an incorporation reaction mixture includes a catalytic metal ion, a monovalent metal cation, glutamate ions, or a combination thereof.

There is flexibility in the nature of the nucleotide used in the incorporation step. For example, a useful nucleotide can include a 3'-oxygen, which can be, for example, a member of a free 3'-hydroxyl group. Optionally, the 3' position of a nucleotide molecule is modified to include a 3' terminator moiety. The 3' terminator moiety may be a reversible terminator or may be an irreversible terminator. Optionally, the reversible terminator nucleotide includes a 3'-$ONH_2$ moiety attached at the 3' position of the sugar moiety. For example, U.S. Pat. Nos. 7,544,794 and 8,034,923 (the disclosures of these patents are incorporated herein by reference) describe reversible terminators in which the 3'-OH group is replaced by a 3'-$ONH_2$ moiety. Optionally, the reversible terminator of the at least one nucleotide molecule is replaced or removed before or after the examination step. Further examples of useful reversible terminator moieties are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference Nucleotides (e.g., incorporable nucleotides that are neither reversible terminator nucleotides, nor irreversible terminator nucleotides) present in the reaction mixture but not sequestered in a ternary complex may cause multiple nucleotide insertions during an incorporation reaction. A wash step can be employed prior to the chemical incorporation step to promote or ensure only the nucleotide sequestered within a trapped ternary complex being available for incorporation during the incorporation step. Optionally, free nucleotides may be removed by enzymes such as phosphatases.

Optionally, a nucleotide enclosed within a ternary complex of an examination step is incorporated into the 3'-end of the template nucleic acid primer during a subsequent incorporation step. Alternatively, the incorporation step involves replacing a nucleotide from the examination step and incorporating another nucleotide into the 3'-end of the template nucleic acid primer. The incorporation step can involve releasing a nucleotide from within a ternary complex and incorporating a nucleotide of a different kind into the 3'-end of the primer of the primed template nucleic acid molecule. Optionally, the released nucleotide is removed and replaced with an incorporation reaction mixture containing a next correct nucleotide. For example, the incorporated nucleotide can be a reversible terminator nucleotide, such as an unlabeled reversible terminator nucleotide that does not include a detectable fluorophore. In this example, the reversible terminator nucleotide can replace a non-blocked nucleotide, such as a labeled non-blocked nucleotide, that had been present in an examination step.

Suitable reaction conditions for incorporation may involve replacing the examination reaction mixture with an incorporation reaction mixture. Optionally, nucleotide(s) present in the examination reaction mixture are replaced with one or more nucleotides in the incorporation reaction mixture. Optionally, the polymerase(s) present during the examination step is replaced during the incorporation step. By this approach it is possible to employ different types of polymerase in the examination and incorporation steps. Optionally, the polymerase present during the examination step is modified during the incorporation step. Optionally, the one or more nucleotides present during the examination step are modified during the incorporation step. The reaction mixture and/or reaction conditions present during the examination step may be altered by any means during the incorporation step. These means include, but are not limited to, removing reagents, chelating reagents, diluting reagents, adding reagents, altering reaction conditions such as conductivity or pH, and any combination thereof.

The disclosed methods related to Sequencing by Binding™ methods do not require a label (e.g., a FRET partner)

to be present on the polymerase, the primed template nucleic acid, or the nucleotide sequestered within a ternary complex. Alternatively, a FRET partner can be present on a polymerase having a sequence set forth herein. The FRET partner can be positioned to interact with a FRET partner on a primer, template or nucleotide. The FRET partner that is attached to the polymerase can be a donor or acceptor in a FRET interaction.

A polymerase may be unlabeled, or may not generate any signal when the polymerase is used for identifying cognate or non-cognate nucleotide in a method set forth herein. However, the polymerase can include a covalently attached detectable label, such as a fluorescent label, a Raman scattering tag, etc. The polymerase preferably does not transfer energy to any labeled nucleotide to render it detectable by the detection apparatus used for carrying out the technique. The label or dye of the detectable nucleotide(s) or polymerase(s) employed in the procedure preferably is not an intercalating dye (e.g., as disclosed in U.S. Pat. No. 8,399,196), nor does it need to change its signal-generating properties (e.g., fluorescent output) upon binding DNA. A label or dye present on a labeled nucleotide need not be a conformationally sensitive dye that changes spectral properties when it is the cognate nucleotide present in a ternary complex. Optionally, a polymerase includes a detectable label, but the label is not detected in the method set forth herein.

The next correct nucleotide can be identified before an incorporation step, thereby allowing the incorporation step to avoid the use of labeled reagents and/or monitoring. Optionally, nucleotides used for identifying the next correct nucleotide are free of attached detectable tags or labels. Indeed, sometimes none of the nucleotides in the procedure contains a detectable label. Optionally, a nucleotide includes a detectable label, but the label is not detected in the method set forth herein. Optionally, when fluorescently labeled nucleotides are used for determining identity of the next correct nucleotide, the fluorescent label shows substantially no change in detected fluorescent properties as the result of interaction with any nucleotide (e.g., through base pairing in a ternary complex), or as the result of a conformational change to the polymerase itself. Thus, for example, monitoring in a method set forth herein does not require energy transfer to or from the detectable label because of nucleotide interaction with the polymerase. Optionally, the detectable label of a distinguishably labeled polymerase is a fluorescent label, but the fluorescent label is not an intercalating dye that changes properties upon binding a primed template nucleic acid molecule.

A polymerase of the present disclosure can be labeled with a fluorescent detectable label, where the detectable label shows substantially no change in its fluorescent properties (excitation and emission) as the result of interaction with any nucleotide, or as the result of a conformational change to the polymerase itself. Thus, for example, labeled polymerase signaling need not require energy transfer to or from the detectable label because of nucleotide interaction with the polymerase. Optionally, the detectable label of a distinguishably labeled polymerase is a fluorescent label, but the fluorescent label is not an intercalating dye that changes properties upon binding a primed template nucleic acid molecule. Optionally, a polymerase having a sequence set forth herein can be attached to a nucleic acid intercalating dye. Exemplary intercalating dyes and methods for their use are set forth, for example, in U.S. Pat. No. 8,399,196, which is incorporated herein by reference.

An examination step of a sequencing reaction may be repeated 1, 2, 3, 4 or more times prior to performing an incorporation step. Moreover, the combination of nucleotides used for examination during an individual cycle can differ from each other such that the net result of the different deliveries and examinations is to produce a series of signals that encode a particular nucleotide type. In some embodiments, an examination step is carried out in a way that the identity of at least one nucleotide type is imputed. Alternatively or additionally to using imputation, an examination step can use disambiguation to identify one or more nucleotide types. Exemplary methods that employ imputation, disambiguation or encoding schemes are set forth in U.S. Pat. No. 9,951,385 and U.S. patent application Ser. No. 15/922,787, each of which is incorporated herein by reference.

Reaction Mixtures

Reaction mixtures for sequencing or other methods can include one or more reagents that are commonly present in polymerase-based nucleic acid synthesis reactions. Reaction mixture reagents include, but are not limited to, enzymes (e.g., polymerase(s)), dNTPs (or analogs thereof), template nucleic acids, primer nucleic acids (e.g. including 3' blocked primers), salts, buffers, small molecules, co-factors, metals, and ions. The ions may be catalytic ions, divalent catalytic ions, non-catalytic ions, non-covalent metal ions, or a combination thereof. The reaction mixture can include salts, such as NaCl, KCl, potassium acetate, ammonium acetate, potassium glutamate, $NH_4Cl$, or ($NH_4HSO_4$), that ionize in aqueous solution to yield monovalent cations. The reaction mixture can include a source of ions, such as $Mg^{2+}$ or $Mn^{2+}$, $Co^{2+}$, $Cd^{2+}$ or $Ba^{2+}$ ions. The reaction mixture can include tin, $Ca^{2+}$, $Zn^{2+}$, $Cu^{2+}$, $Co^{2+}$, $Fe^{2+}$ (e.g., $Fe(II)SO_4$), or $Ni^{2+}$, or other divalent or trivalent non-catalytic metal cation that stabilizes ternary complexes by inhibiting formation of phosphodiester bonds between the primed template nucleic acid molecule and the cognate nucleotide. Other metals may also be present such as lithium, sodium or potassium.

Buffers include, but are not limited to, Tris, Tricine, HEPES, MOPS, ACES, MES, phosphate-based buffers, and acetate-based buffers. Reaction mixtures can include chelating agents such as EDTA, EGTA, and the like. Optionally, reaction mixtures include cross-linking reagents. Optionally, an examination mixture comprises a high concentration of salt; a high pH; 1, 2, 3, 4, or more types of nucleotides; potassium glutamate; a chelating agent; a polymerase inhibitor; a catalytic metal ion; a non-catalytic metal ion; or any combination thereof. The first reaction mixture can include 10 mM to 1.6 M of potassium glutamate (including any amount between 10 mM and 1.6 M). Optionally, the incorporation reaction mixture comprises a catalytic metal ion; 1, 2, 3, 4, or more types of nucleotides; potassium chloride; a non-catalytic metal ion; or any combination thereof.

The provided methods can be conducted under reaction conditions and using reaction mixtures that modulate the formation and stabilization of a ternary complex during an examination step. The reaction conditions of the examination step typically favor the formation and/or stabilization of a ternary complex encapsulating a nucleotide and hinder the formation and/or stabilization of a binary complex. The binary interaction between the polymerase and template nucleic acid may be manipulated by modulating sequencing reaction parameters such as ionic strength, pH, temperature, or any combination thereof, or by the inclusion of a binary complex destabilizing agent in reaction mixtures. Optionally, high salt (e.g., 50 to 1,500 mM) and/or pH changes are utilized to destabilize a binary complex. Optionally, a binary complex may form between a polymerase and a template nucleic acid during the examination or incorporation step of the sequencing reaction, regardless of the presence of a nucleotide. Optionally, the reaction conditions favor the stabilization of a ternary complex and destabilization of a binary complex. By way of example, the pH of the examination reaction mixture can be adjusted from 4.0 to 10.0 to favor the stabilization of a ternary complex and destabilization of a binary complex. Optionally, the pH of the examination reaction mixture is from 4.0 to 6.0. Optionally, the pH of the examination reaction mixture is 6.0 to 10.0.

Reaction mixtures are provided for methods of formation and/or stabilization of a ternary complex comprising a polymerase bound to a primed template nucleic acid and a nucleotide enclosed within the polymerase-template nucleic acid complex, under examination reaction conditions. Examination reaction conditions may preclude or attenuate nucleotide incorporation. Optionally, incorporation of the enclosed nucleotide is precluded and the complex is stabilized or trapped in a pre-chemistry conformation or a ternary complex. Optionally, the enclosed nucleotide is incorporated and a subsequent nucleotide incorporation is inhibited. In this instance, the complex may be stabilized or trapped in a pre-translocation conformation. For the sequencing reactions provided herein, the ternary complex is stabilized during the examination step, allowing for controlled nucleotide incorporation. Optionally, a stabilized ternary complex is a complex wherein incorporation of an enclosed nucleotide is attenuated, either transiently (e.g., to examine the complex and then incorporate the nucleotide) or permanently (e.g., for examination only) during an examination step.

Optionally, the examination reaction mixtures comprise a plurality of primed template nucleic acids, polymerases, nucleotides, or any combination thereof. Optionally, the plurality of nucleotides comprises at least 1, 2, 3, 4, or more types of different nucleotides, for example dATP, dTTP (or dUTP), dGTP, and dCTP. Alternatively or additionally, the plurality of nucleotides comprises at most 1, 2, 3, or 4 types of different nucleotides, for example dATP, dTTP (or dUTP), dGTP, and dCTP. Optionally, the plurality of nucleotides comprises one or more types of nucleotides that, individually or collectively, complement at least 1, 2, 3 or 4 types of nucleotides in a template, for example dATP, dTTP (or dUTP), dGTP, or dCTP. Alternatively or additionally, the plurality of nucleotides comprises one or more types of nucleotides that, individually or collectively, complement at most 1, 2, 3 or 4 types of nucleotides in a template, for example dATP, dTTP (or dUTP), dGTP, or dCTP. Optionally, the plurality of template nucleic acids is a clonal population of template nucleic acids.

Useful Nucleotide Analogs

Optionally, a ternary complex of an examination step comprises either a native nucleotide, non-natural nucleotide analog or modified nucleotide to facilitate stabilization of the ternary complex. Optionally, a nucleotide analog comprises a nitrogenous base, five-carbon sugar, and phosphate group; wherein any moiety of the nucleotide may be modified, removed and/or replaced. Nucleotide analogs may be non-incorporable nucleotides. Non-incorporable nucleotides may be modified to become incorporable at any point during the sequencing method.

Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein.

Nucleotide analogs can include terminators that reversibly prevent nucleotide incorporation at the 3'-end of the primer. One type of reversible terminator is a 3'-O-blocked reversible terminator. Here the terminator moiety is linked to the oxygen atom of the 3'-OH end of the 5-carbon sugar of a nucleotide. For example, U.S. Pat. Nos. 7,544,794 and 8,034,923 (the disclosures of these patents are incorporated by reference) describe reversible terminator dNTPs having the 3'-OH group replaced by a 3'-$ONH_2$ group. Another type of reversible terminator is a 3'-unblocked reversible terminator, wherein the terminator moiety is linked to the nitrogenous base of a nucleotide. For example, U.S. Pat. No. 8,808,989 (the disclosure of which is incorporated by reference) discloses particular examples of base-modified reversible terminator nucleotides that may be used in connection with the methods described herein. Other reversible terminators that similarly can be used in connection with the methods described herein include those described in U.S. Pat. Nos. 7,956,171, 8,071,755, and 9,399,798 (the disclosures of these U.S. patents are incorporated by reference). For reviews of nucleotide analogs having terminators see e.g., Mu, R., et al., "The History and Advances of Reversible Terminators Used in New Generations of Sequencing Technology," Genomics, Proteomics & Bioinformatics 11(1):34-40 (2013). Optionally, one or more native nucleotides employed during the examination step is replaced by a second type of nucleotide that is incorporated during the incorporation step. For example, nucleotides present in the reaction mixture used during an examination step may be replaced by nucleotide analogs that include reversible terminator moieties (e.g., positioned on the base or sugar of the nucleotide molecule).

Optionally, nucleotide analogs have terminator moieties that irreversibly prevent nucleotide incorporation at the 3'-end of the primer. Irreversible nucleotide analogs include 2',3'-dideoxynucleotides, ddNTPs (ddGTP, ddATP, ddTTP, ddCTP). Dideoxynucleotides lack the 3'-OH group of dNTPs that is essential for polymerase-mediated synthesis. Nucleotide analogs having irreversible terminator moieties can be particularly useful for genotyping and allele capture methods such as those set forth herein or in U.S. Pat. App. Pub. No. 2017/0022553 A1 or U.S. Pat. No. 9,932,631, each of which is incorporated herein by reference.

Optionally, non-incorporable nucleotides comprise a blocking moiety that inhibits or prevents the nucleotide from forming a covalent linkage to a second nucleotide (3'-OH of a primer) during the incorporation step of a nucleic acid polymerization reaction. In certain embodiments, the blocking moiety can be removed from the nucleotide, allowing for nucleotide incorporation.

Any nucleotide modification that traps a polymerase in a ternary complex may be used in the methods disclosed herein. The nucleotide may be trapped permanently or transiently. Optionally, the nucleotide analog is not the means by which a ternary complex is stabilized. Any ternary complex stabilization method may be combined in a reaction utilizing a nucleotide analog.

Optionally, a nucleotide analog that allows for the stabilization of a ternary complex is combined with reaction conditions that usually release the ternary complex. The conditions include, but are not limited to, the presence of a release reagent (e.g., catalytic metal ion, such as magnesium or manganese). Optionally, the ternary complex is stabilized even in the presence of a catalytic metal ion. Optionally, the ternary complex is released even in the presence of a nucleotide analog. Optionally, the stabilization of the ternary complex is dependent, in part, on the concentrations and/or identity of the stabilization reagent and/or release reagents, and any combination thereof. Optionally, the stabilization of a ternary complex using nucleotide analogs is combined with additional reaction conditions that function to stabilize a ternary complex, including, but not limited to, sequestering, removing, reducing, omitting, and/or chelating a catalytic metal ion; the presence of a polymerase inhibitor, cross-linking agent; and any combination thereof.

Optionally, one or more nucleotide analogs can be labeled with distinguishing and/or detectable tags or labels. The tags or labels can be detected, for example, in a method set forth herein. However, in particular embodiments such tags or labels preferably are not detected during examination, identification of the base or incorporation of the base, and such tags or labels are not detected during the sequencing methods disclosed herein. The tags may be distinguishable by means of their differences in fluorescence, Raman spectrum, charge, mass, refractive index, luminescence, length, or any other measurable property such as those set forth herein or in references cited herein. The tag may be attached to one or more different positions on the nucleotide, so long as the fidelity of binding to the polymerase-nucleic acid complex is sufficiently maintained to enable identification of the complementary base on the template nucleic acid correctly. Optionally, the tag is attached to the nucleobase of the nucleotide. Under suitable reaction conditions, the tagged nucleotides may be enclosed in a ternary complex with the polymerase and the primed template nucleic acid. Alternatively, a tag is attached to the gamma phosphate position of the nucleotide.

Useful Polymerase Compositions

Identification of a cognate nucleotide may employ use of a unique polymerase composition (e.g., a reagent including a polymerase, such as a detectably labeled polymerase) and a single nucleotide (e.g., a native nucleotide). Optionally, a single type of labeled polymerase is used in combination with different nucleotides, one at a time, to create unique combinations. Alternatively, more than one distinguishably labeled polymerase can be used to create the unique polymerase-nucleotide combinations. While individually labeled polymerases may be used for each different nucleotide used in an examination step, mixtures of two different labeled polymerases alternatively can be used as a single unique polymerase composition. Generally speaking, the primer strand of a primed template nucleic acid molecule undergoing examination is chemically unchanged by the polymerase or any other enzyme during examination procedure that identifies the cognate nucleotide. This is to say that the primer is neither extended by formation of a new phosphodiester bond, nor shortened by nucleolytic degradation during the examination step to identify the next correct nucleotide.

Polymerases and nucleotides can be combined in various ways to form different polymerase compositions. For example, the same labeled polymerase can be used in combination with two different nucleotides to yield two different polymerase-nucleotide combinations. By way of another example, a polymerase having two or more distinguishable labels or a mixture of the same distinguishably labeled polymerases (i.e., representing a third distinct polymerase composition) can be used in combination with a third nucleotide to yield a third polymerase-nucleotide combination. Alternatively or additionally, an unlabeled polymerase can be used in combination with a fourth nucleotide to yield a fourth polymerase-nucleotide combination (i.e., a "dark" combination).

Optionally, a polymerase employed during an examination step includes an exogenous detectable label (e.g., a fluorescent label, Raman scattering tag or other label set forth herein) chemically linked to the structure of the polymerase by a covalent bond after the polymerase has been at least partially purified using protein isolation techniques. For example, the exogenous detectable label can be chemically linked to the polymerase using a free sulfhydryl or a free amine moiety of the polymerase. This can involve chemical linkage to the polymerase through the side chain of a cysteine residue, or through the free amino group of the N-terminus. A fluorescent label attached to the polymerase can be useful for locating the polymerase, as may be important for determining whether or not the polymerase has localized to a feature or spot on an array corresponding to immobilized primed template nucleic acid. The fluorescent signal need not, and preferably does not change absorption or emission characteristics as the result of binding any nucleotide. For example, the signal emitted by the labeled polymerase can be maintained substantially uniformly in the presence and absence of any nucleotide being investigated as a possible next correct nucleotide.

A common method of introducing a label on a polymerase involves chemical conjugation to amines or cysteines present in the non-active regions of the polymerase. Such conjugation methods are well known in the art. As non-limiting examples, n-hydroxysuccinimide esters (NHS esters) are commonly employed to label amine groups that may be found on an enzyme. Cysteines readily react with thiols or maleimide groups, while carboxyl groups may be reacted with amines by activating them with EDC (1-Ethyl-3-[3-dimethylaminopropyl]carbodiimide hydrochloride). Optionally, N-Hydroxysuccinimide (NETS) chemistry is employed at pH ranges where only the N-terminal amines are reactive (for instance, pH 7), such that only a single tag is added per polymerase.

Use of Polymerase Inhibitors to Stabilize Ternary Complexes

A ternary complex may be formed and/or stabilized by including a polymerase inhibitor in the examination reaction mixture. Inhibitor molecules phosphonoacetate, (phosphonoacetic acid) and phosphonoformate (phosphonoformic acid, common name Foscarnet), Suramin, Aminoglycosides, INDOPY-1 and Tagetitoxin are non-limiting examples of uncompetitive or noncompetitive inhibitors of polymerase activity. The binding of the inhibitor molecule can be used to stabilize the polymerase in its ternary complex conformation before or after the incorporation of a nucleotide, and forcing the polymerase to be bound to the template nucleic acid until the inhibitor molecules are not available in the reaction mixture by removal, dilution or chelation.

Stabilized Ternary Complexes

Provided herein are stabilized ternary complexes. The complexes include an engineered polymerase described herein, a primer-template nucleic acid hybrid and a next correct nucleotide for the primed template nucleic acid. Optionally, a blocking group is located at the 3' end of the primer. Optionally, the stabilized ternary complex further includes an inhibitory cation. The stabilized ternary complex may include a polymerase inhibitor. Optionally, the stabilized ternary complex lacks a catalytic metal ion. The next correct nucleotide and/or polymerase can optionally include an exogenous label. The ability to form and maintain ternary complexes (e.g., produced using four different polymerase-nucleotide combinations in serial fashion) on different features of an array can be facilitated by stabilization of ternary complexes. This can be accomplished in a variety of ways.

Optionally, the stabilized ternary complex comprises one or more of polymerase inhibitors; non-catalytic cations; aptamers; anti-polymerase antibodies; and a reversibly blocked primed template nucleic acid molecule (i.e., a non-extendible primer). Thus, stabilized ternary complexes including a primed template nucleic acid, polymerase, and cognate nucleotide can include non-catalytic metal ions. Non-catalytic metal ions include, but are not limited to, $Cu^{2+}$, $Mn^{2+}$, $V^{5+}$, $Eu^{5+}$, $Ni^{2+}$, $Sr^{2+}$, $Tb^{3+}$, $Ca^{2+}$ and $Co^{2+}$. Optionally, the non-catalytic metal ions include trivalent lanthanide ions, including europium ions and terbium ions. Optionally, the stabilized ternary complex includes a blocked primer terminating at its 3'-end.

Systems

The disclosed technique for determining cognate nucleotides using engineered polymerases, whether for a single nucleic acid feature or for a population of different nucleic acid features spaced apart in a flow cell or well of a multiwell plate, can be performed using a dedicated system of interrelated modules or components. Some useful systems will be familiar to those having an ordinary level of skill in the art, and can be adapted or configured for processing by the disclosed technique that relies on identification or tracking of distinguishably labeled polymerases. An exemplary system for use in identifying a next correct nucleotide of a primed template nucleic acid molecule typically will include: a reaction vessel; a reagent dispense module; an imaging module; a processing module; and an electronic storage device. Systems useful for single-scan imaging of a population of nucleic acid features will have the capability of detecting four different fluorescent emission wavelengths. Essential features of particularly preferred systems are described below.

The reaction vessel employed in the system may take different forms. The reaction vessel can be placed in fluid communication with a supply of one or engineered polymerases and/or other reagent(s) useful in a method set forth herein. Examples of reaction vessels include flow cells having inlet and outlet ports, and one or more wells of a multiwell plate. A collection or population of nucleic acids to be processed by a method set forth herein can be contained in a reaction vessel. The nucleic acids can be present at features of an array. For example, nucleic acid features may be "clusters" of spaced-apart amplified nucleic acids (e.g., in situ amplified nucleic acids). Other features can be individual beads harboring homogenous populations of nucleic acids.

A population of molecules such as nucleic acids, polymerases or the like can be attached to an array such that the molecules at one feature of the array can be distinguished from molecules at other features of the array. An array can include different molecules that are each located at different addressable features on a solid support. Alternatively, an array can include separate solid supports (e.g. beads) each functioning as a feature that bears a different molecule, wherein the different molecules can be identified according to the locations of the solid supports on a surface to which the solid supports are attached, or according to the locations of the solid supports in a liquid such as a fluid stream.

A feature of an array can contain only a single molecule or it can contain a population of several molecules of the same species (i.e. an ensemble of the molecules). Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 microns, 50 microns, 10 microns, 5 microns, 1 micron, or 0.5 micron. Alternatively or additionally, an array can have features that are separated by greater than 0.5 micron, 1 micron, 5 microns, 10 microns, 50 microns or 100 microns. The features can each have an area of less than 1 square millimeter, 500 square microns, 100 square microns, 25 square microns, 1 square micron or less.

In particular embodiments, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different types of polymerases, nucleic acids or ternary complexes are detected in parallel. Although it is also possible to serially process different types of molecules using one or more steps of the methods set forth herein, parallel processing can provide cost savings, time savings and uniformity of conditions. An apparatus or method of the present disclosure can include at least 2, 10, 100, $1\times10^3$, $1\times10^4$, $1\times10^5$, $1\times10^6$, $1\times10^9$, or more different molecules. Alternatively or additionally, an apparatus or method of the present disclosure can include at most $1\times10^9$, $1\times10^6$, $1\times10^5$, $1\times10^4$, $1\times10^3$, 100, 10, 2 or fewer, different molecules. Accordingly, various reagents or products set forth herein (e.g. polymerases, nucleic acids, or ternary complexes) can be multiplexed to have different types or species in these ranges. Different types of molecules (e.g. nucleic acids with different nucleotide sequences) that are present in an array can be located at different features of an array. Thus, signals acquired from a feature will be indicative of a particular nucleic acid sequence present at the feature.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies. Other useful arrays include those that are used in nucleic acid sequencing applications. For example, arrays that are used to attach amplicons of genomic fragments (often referred to as clusters) can be particularly useful. Examples of nucleic acid sequencing arrays that can be used herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A reagent dispense module included in a system herein also may take different forms. The reagent dispense module can be configured to direct into a reaction vessel, one or more of the molecules set forth herein, such as an engineered polymerase. Different reagents can be contained in different reservoirs prior to being dispensed. In some cases, various reagents can be mixed or combined to suit a particular reaction. For example, individual reservoirs can respectively contain mixtures of reagents for ternary complex examination, primer extension, primer deblocking, washing or the like. Optionally, the reaction vessel is a flow cell, and each reagent exchange involves flowing through the flow cell a second liquid reagent to replace a first liquid reagent. Optionally, the reagent dispense module includes a syringe pump that controllably delivers reagents.

An imaging module also may take different form. The imaging module can be configured for detecting ternary complexes, for example, when they are attached to an array. Optionally, the imaging module includes an illumination component and a detection component. Illumination components may take the form of a bulb, filament, laser or light emitting diode (LED) Useful detectors include fluorometers that measure parameters of fluorescence. There also can be one or more optical filters for narrowing the range or band of wavelengths that are transmitted either to a sample or to a detector. The detection component of the imaging module optionally can be configured to detect intensities of a plurality of different wavelengths, each corresponding to a fluorescence emission by one of the several distinguishably labeled reaction components.

A processing module also can take different forms. For example, the processing module can include a computer (e.g., either a standalone computer or processor, a computer or processor integrated into a system within a common housing or chassis) configured with software to compare intensities of the plurality of different wavelengths, and to determine therefrom the identity of the next correct nucleotide that is present in a ternary complex. The processing module can be configured to receive a result from the imaging module, and further configured to identify the next correct nucleotide using the result processed result. Configuring of the processing module may involve embedded, or otherwise accessible software instructions (e.g., being accessed from a remote software repository).

A useful electronic storage device can take different forms. The storage device can be in communication with a processing module, and can store a non-transient record of processed signal data such as normalized signal intensities or a next correct nucleotide identified by the processing module. For example, the electronic storage device can be a computer hard drive, flash drive, floppy disk, compact disk (CD) or other optical disk storage medium, cloud storage arrangement, and the like.

Optionally, a useful system can also include an output device that produces a non-transient record of the next correct nucleotide identified by the processing module. The non-transient record produced by the output device optionally can be either a record stored on computer-readable media, or a record printed on paper.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims.

EXAMPLES

Example 1. Engineered Polymerases for Improved Sequencing by Binding™ Quality

Materials and Methods:

Flow cells containing primed template nucleic acids were prepared as follows.

Template nucleic acid strands synthesized in 12 PCR reactions using 5'-biotinylated primers were prepared, and then independently bound to streptavidin-coated magnetic beads. This resulted in a population of 12 bead types, where each bead harbored a homogenous collection of template strands. Beads used in the procedure had been functionalized with 1 mM NHS-PEG4-TCO in phosphate buffered saline (PBS). Beads harboring immobilized template strands were next flowed over an aminosilane flow cell surface that had been functionalized with tetrazine. The mixture was incubated for one hour to permit covalent attachment of the decorated beads to the functionalized surface within the flow cell. Next, sequencing primers were flowed into the flow cell and allowed to hybridize to the immobilized template strands.

Sequencing was performed by repeated cycles. The sequencing cycle was initiated by incorporating reversible terminator nucleotides at the 3'-ends of the hybridized sequencing primers to create a collection of blocked primed template nucleic acid molecules. This was accomplished by delivery of RTS solution to the flow cell (RTS contained: 50 mM Tricine pH 8.4, 0.1% Tween-80, 35 U/ml DNA polymerase, 5 mM $MgCl_2$, 0.1% hydroxylamine, 50 mM KCl, 0.1 mM EDTA, and 200 nM of unlabeled reversibly terminated nucleotide analogs of dATP, dGTP, dCTP, and dTTP). The reversible terminator nucleotide used in this illustrative procedure included a 3'-$ONH_2$ reversible terminator moiety. A description of this reversible terminator nucleotide can be found in U.S. Pat. No. 7,544,794, the disclosure of which is incorporated herein by reference. The flow cell was then washed with ESB solution (1 M guanidinium thiocyanate, 60 mM HEPES, 0.1% Tween-80, 0.1% hydroxylamine and 2 mM EDTA) followed by a wash with PRE solution (50 mM Tricine pH 8.4, 50 mM KCl, 0.1% Tween-80, 0.1% hydroxylamine and 0.1 mM EDTA).

The cycle then continued with an examination subroutine in which four different nucleotides were sequentially delivered to the flow cell. Reversible terminator moieties on the 3' nucleotides of the primer strands precluded nucleotide incorporation during the ternary complex formation and detection steps. In standard conditions, one of the four different labeled nucleotides was delivered to the flow cell in EXAM solution (Cy5-dNTP (400 nM for each of Cy5-dATP, Cy5-dGTP or Cy5-dCTP; or 800 nM for Cy5-dTTP), 1 mM $MgCl_2$, and 70 U/ml DNA polymerase in IMG solution), followed by a wash with IMG solution (20 mM Tricine pH 7.0, 3% sucrose, 1M betaine, 50 mM LiCl, 0.1% Tween-80, 50 mM KCl, 10 mM ammonium sulfate, 0.1% hydroxylamine, and 0.1 mM EDTA). The Cy5-dNTP nucleotides are described in US Publication No. 2018/0208983, which is incorporated herein by reference. The flow cell was imaged via fluorescence microscopy to detect ternary complexes that were retained in the IMG solution. Following imaging the flow cell was washed with ESB solution and then with PRE solution. The steps of the subroutine were repeated for each of the four nucleotide types individually. The examination subroutine was modified in several experiments as set forth below in the context of the figures.

Following the examination subroutine, the sequencing cycle continued with removal of the reversible terminator moiety from the primers by treating the flow cell the solution containing 0.25 M sodium acetate and 0.7 M sodium nitrite titrated to pH 4.8 with acetic acid. The flow cell was then washed in PRE solution to remove the sodium acetate and sodium nitrite. The sequencing process then returned to the sequencing cycle initiation step.

Figure 2:
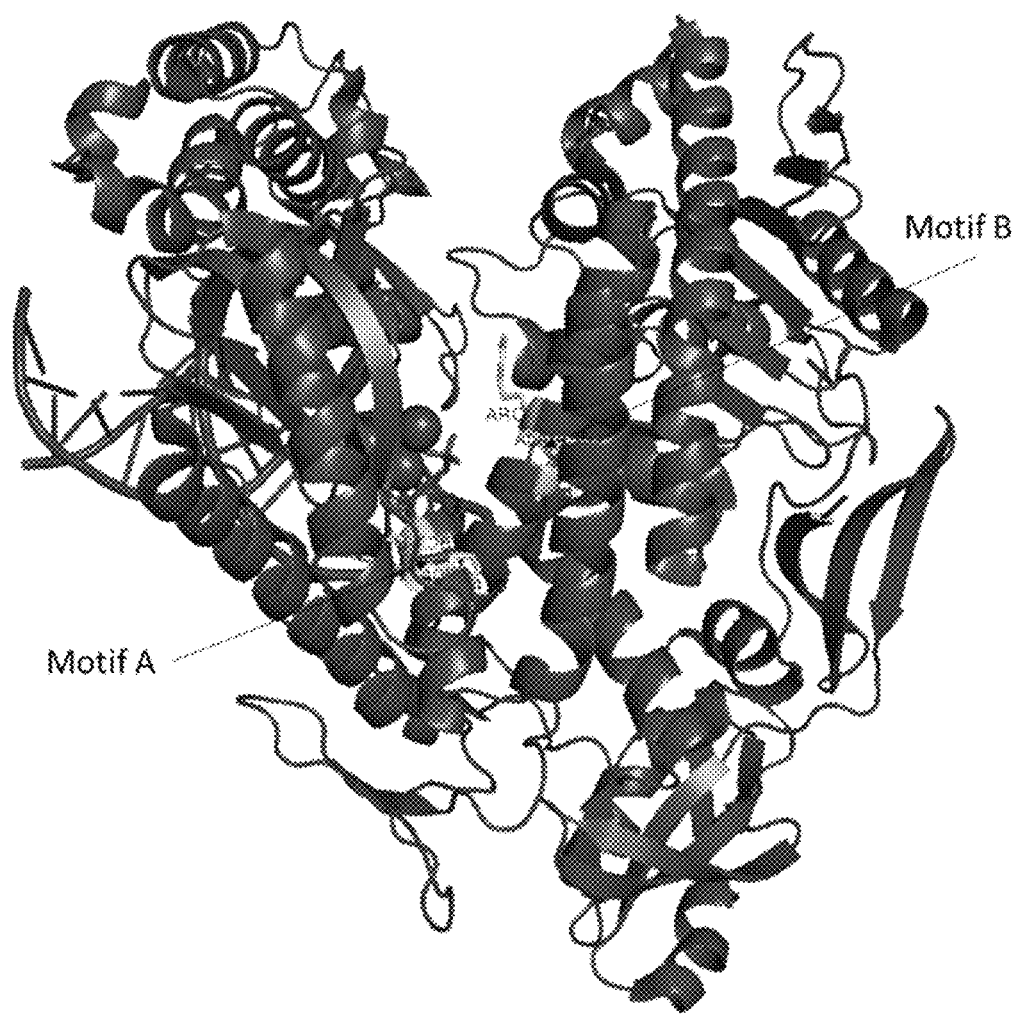
FIG. 2 is a schematic showing the crystal structure of KOD polymerase (SEQ ID NO:2) and showing Motif A and Motif B of the polymerase.

Terminator™ was the wild type (WT) polymerase used for mutagenesis studies and having the amino acid sequence in SEQ ID NO:1. Residues at amino acid positions L408, Y409, and P410 in Motif A sequence of Terminator™ (THM) sequence were altered and selected engineered polymerases were tested for the Sequencing By Binding™ performance compared to THM. Additionally, engineered polymerases with modifications at R484, L485, and I486 positions in the Motif B sequence were also tested for the Sequencing By Binding™ performance compared to THM. Table 1 is a list of engineered polymerases. FIG. 1 shows the crystal structure of 9° N DNA polymerase (Protein Database Code: 5OMQ), the parent polymerase of Terminator, with the Motif A and Motif B residues. FIG. 2 shows the crystal structure of KOD polymerase (Protein Database Code: 5OMF) with the Motif A and Motif B residues.

TABLE 1

List of Engineered Polymerases.

| Engineered Polymerase Name | Mutations |
|---|---|
| M01 | R484F I486L |
| M03 | I486V |
| M05 | R484I L485K I486R |
| M06 | L485H I486H |

TABLE 1-continued

List of Engineered Polymerases.

| Engineered Polymerase Name | Mutations |
|---|---|
| M07 | R484A L485D I486R (also contains K240R) |
| M08 | R484L |
| M09 | R484S L485T I486L |
| M10 | R484Q L485T I486F |
| M11 | R484T I486V |
| M12 | R484K L485T I486F |
| M13 | R484L L485N I486R |
| M14 | L485W I486G |
| M15 | L408F Y409F P410T |
| M16 | L408F Y409H P410V |
| M17 | R484S L485F I486R |

Results:

Tables 2 and 3 show a summary of polymerase mutant sequencing data compared to the WT polymerase THM. All the sequencing metrics were recorded and summarized for comparison purposes. Sequencing experiments were done for 50, 100 or 150 cycles for each engineered polymerase. The formulas that were used for sequencing metrics are shown below:

Average error rate=Number_of_non-N_Errors/(Number_of_non-N_Errors+Number_of_non-N_Correct)*100 at each cycle, where nan is used if the denominator is 0 due to all calls being N.

Extracted_Intensity_Sum_P50_Fit_Tau=The mean lifetime, Tau, from a fit to Extracted_Intensity_Sum_P50 of the form A*exp(−cycle/Tau)

This number represents the average Tau for all four exams.

On_Called_Intensity_P50_A_Fit_Tau=The mean lifetime, Tau, from a fit to On_Called_Intensity_P50_A of the form A*exp(−cycle/Tau)

This number represents the Tau for A exam only.

On_Called_Intensity_P50_A_Fit_R_Squared=R Squared from a fit to On_Called_Intensity_P50_A of the form A*exp (−cycle/Tau)

This number represents the $R^2$ value for A exam only. The remaining 3 exams; G, C and T have their own Tau (τ) and $R^2$ values.

Higher Tau (τ) is indicative of slower rate of signal decay, which is generally preferred for increased read length and sequencing accuracy, whereas faster rate of signal decay is characterized by lower values for τ. The goodness of fit was calculated as the coefficient of determination, $R^2$. Higher $R^2$ values correlate with reduced signal intensity variance from variability in sequence context, whereas an increase in adverse impact of sequence context results in a lower $R^2$ value.

Average purity=2*(I1/(I1+I2))−0.5 at each cycle, where I1 is the intensity of the brightest exam and I2 is the intensity of the second brightest exam, which have both had the minimum exam intensity subtracted.

TABLE 2

Sequencing summary data for various polymerase mutants compared to WT THM.

| Polymerase Name | THM | M05 | M17 | M08 | M11 | M12 | M06 | M01 |
|---|---|---|---|---|---|---|---|---|
| Number_of_Cycles | 100 | 50 | 100 | 100 | 100 | 100 | 100 | 100 |
| Average_Error_Rate_C20 | 0.19 | 0.00 | 0.11 | 0.05 | 0.13 | 0.54 | 0.11 | 0.01 |
| Average_Error_Rate_C30 | 0.13 | 0.01 | 0.08 | 0.04 | 0.25 | 0.61 | 0.14 | 0.09 |
| Average_Error_Rate_C40 | 0.1 | 0.01 | 0.06 | 0.04 | 0.29 | 0.49 | 1.17 | 0.11 |
| Average_Error_Rate_C50 | 0.08 | 0.00 | N/A | 0.03 | 0.46 | 0.46 | 2.67 | 0.14 |

TABLE 2-continued

Sequencing summary data for various polymerase mutants compared to WT THM.

| Polymerase Name | THM | M05 | M17 | M08 | M11 | M12 | M06 | M01 |
|---|---|---|---|---|---|---|---|---|
| Average_Error_Rate_C100 | 0.75 | N/A | 0.36 | 0.55 | 4.49 | 1.34 | 17.64 | 0.44 |
| Average_Error_Rate_C150 | N/A | N/A | N/A | N/A | N/A | N/A | N/A | N/A |
| Extracted_Intensity_Sum_P50_Fit_Tau | 120.4 | 77.6 | 126.6 | 116.2 | 112.2 | 126.9 | 111.1 | 91.0 |
| On_Intensity_P50_A_Fit_Tau | 51.3 | 35.0 | 46.8 | 50.9 | 44.9 | 56.3 | 39.6 | 62.8 |
| On_Called_Intensity_P50_A_Fit_R_Squared | 0.95 | N/A | N/A | 0.97 | 0.88 | 0.84 | 0.94 | 0.94 |
| On_Intensity_P50_G_Fit_Tau | 53.5 | 37.8 | 50 | 51.6 | 48.3 | 65.1 | 38.8 | 64.3 |
| On_Called_Intensity_P50_G_Fit_R_Squared | 0.94 | N/A | N/A | 0.96 | 0.81 | 0.79 | 0.95 | 0.94 |
| On_Intensity_P50_C_Fit_Tau | 53.7 | 32.3 | 46.2 | 50.3 | 43 | 56.9 | 36.7 | 60.7 |
| On_Called_Intensity_P50_C_Fit_R_Squared | 0.94 | N/A | N/A | 0.98 | 0.83 | 0.79 | 0.95 | 0.91 |
| On_Intensity_P50_T_Fit_Tau | 53 | 35.1 | 45.9 | 52.5 | 49.4 | 66 | 37.2 | 65.1 |
| On_Called_Intensity_P50_T_Fit_R_Squared | 0.95 | N/A | N/A | 0.96 | 0.84 | 0.83 | 0.94 | 0.92 |
| Average_Purity_C20 | 0.92 | 0.85 | 0.9 | 0.92 | 0.92 | 0.92 | 0.89 | 0.91 |
| Average_Purity_C30 | 0.91 | 0.83 | 0.89 | 0.91 | 0.9 | 0.91 | 0.87 | 0.90 |
| Average_Purity_C40 | 0.9 | 0.81 | 0.87 | 0.9 | 0.88 | 0.9 | 0.83 | 0.90 |
| Average_Purity_C50 | 0.9 | 0.79 | N/A | 0.88 | 0.87 | 0.9 | 0.8 | 0.89 |
| Average_Purity_C100 | 0.83 | N/A | 0.78 | 0.82 | 0.8 | 0.86 | 0.72 | 0.86 |
| Average_Purity_C150 | N/A | N/A | N/A | N/A | N/A | N/A | N/A | N/A |

N/A: Not applicable

Table 1 shows data for 100 cycle runs except M05 mutant polymerase with a 50 cycle run. M05 showed the lowest error rate at cycle 50 of the engineered polymerases tested. In addition to M05, M08 showed lower 50 cycle error rate than the WT THM. Among the 100 cycle runs, M17, M01 and M08 mutants showed lower error rates than WT THM. Further, M17 had 0.36 error rate at 100 cycle, which was 2.1 fold less than WT THM.

The average Tau metric, Extracted_Intensity_Sum_P50_Fit_Tau, is higher for M17 and M12 compared to WT THM, which represents less signal decay for these engineered polymerases. On the other hand, the individual exam tau, On_Called_Intensity_P50_A_Fit_Tau, values are higher for M12 and M01 compared to WT THM. The individual R2 values per exam are similar between WT THM and M08 and M06.

Purity values were similar for all mutants and the values were comparable to WT THM.

Table 3. 150 cycle sequencing summary data for various polymerase mutants compared to WT THM.

Table 3 shows all the completed 150 cycle runs for WT THM and M16, M17, M15 and M03 engineered polymerases. All engineered polymerases showed lower error rate values at cycle 150 compared to WT THM. Specifically, M15 has the smallest error rate with 0.62 at cycle 150, which is 12.9-fold lower than the WT THM. Additionally, all engineered polymerases showed higher average Tau values compared to WT THM. M17 had the highest average Tau value, which was 1.37-fold higher than WT THM, and the highest individual exam Tau values as well. M15 and M03 showed higher individual R2 values per exam than WT THM. While the engineered polymerases differed in one or more characteristics from WT THM, M15 was the most active polymerase with highest performance and best sequencing metrics.

Example 2

Sequencing with M15 and Therminator™ Polymerases

This example provides a comparison of nucleic acid sequencing using different polymerases. The comparison

| Polymerase Name | THM | M16 | M17 | M15 | M03 |
|---|---|---|---|---|---|
| Number_of_Cycles | 150 | 150 | 150 | 150 | 150 |
| Average_Error_Rate_C20 | 0.08 | 0.2 | 0.12 | 0 | 0 |
| Average_Error_Rate_C30 | 0.1 | 0.13 | 0.09 | 0.04 | 0.01 |
| Average_Error_Rate_C40 | 0.08 | 0.1 | 0.08 | 0.03 | 0.01 |
| Average_Error_Rate_C50 | 0.11 | N/A | N/A | N/A | 0.01 |
| Average_Error_Rate_C100 | 1.67 | N/A | N/A | N/A | 0.11 |
| Average_Error_Rate_C150 | 7.99 | 2.2 | 1.66 | 0.62 | 3.03 |
| Extracted_Intensity_Sum_P50_Fit_Tau | 106 | 121.6 | 145 | 109.3 | 110.7 |
| On_Intensity_P50_A_Fit_Tau | 46.4 | 45.2 | 61.1 | 50.9 | 52.1 |
| On_Called_Intensity_P50_A_Fit_R_Squared | 0.95 | N/A | N/A | 0.98 | 0.97 |
| On_Intensity_P50_G_Fit_Tau | 48.9 | 47.8 | 67.6 | 52.3 | 52.3 |
| On_Called_Intensity_P50_G_Fit_R_Squared | 0.95 | N/A | N/A | 0.98 | 0.97 |
| On_Intensity_P50_C_Fit_Tau | 43.9 | 43.9 | 62.8 | 51.2 | 52.8 |
| On_Called_Intensity_P50_C_Fit_R_Squared | 0.95 | N/A | N/A | 0.98 | 0.97 |
| On_Intensity_P50_T_Fit_Tau | 47.7 | 45.7 | 63.6 | 51.6 | 53.4 |
| On_Called_Intensity_P50_T_Fit_R_Squared | 0.95 | N/A | N/A | 0.98 | 0.98 |
| Average_Purity_C20 | 0.93 | 0.9 | 0.92 | 0.93 | 0.92 |
| Average_Purity_C30 | 0.92 | 0.89 | 0.9 | 0.93 | 0.92 |
| Average_Purity_C40 | 0.9 | 0.87 | 0.88 | 0.92 | 0.91 |
| Average_Purity_C50 | 0.89 | N/A | N/A | N/A | 0.9 |
| Average_Purity_C100 | 0.81 | N/A | N/A | N/A | 0.86 |
| Average_Purity_C150 | 0.74 | 0.69 | 0.63 | 0.85 | 0.8 |

N/A: Not applicable demonstrated the quality of sequencing data obtained using engineered polymerase, M15 (SEQ ID NO:4) was superior to the quality of sequencing data obtained using Therminator™ polymerase.

Materials and Methods:

Flow cells containing primed template nucleic acids were prepared by synthesizing template nucleic acid strands in 12 separate PCR reactions and independently binding the templates to beads. This resulted in a population of 12 bead types, where each bead harbored a homogenous collection of one of the 12 template strands. Beads harboring immobilized template strands were next attached to the inner surface of a flow cell. Sequencing primers were then flowed into the flow cell and allowed to hybridize to the immobilized template strands to form immobilized primer-template hybrids.

Sequencing was performed cyclically, where each cycle included steps for (i) extension: polymerase catalyzed addition of a reversibly terminated nucleotide to the primers of the immobilized primer-template hybrids, (ii) examination: forming and detecting stabilized ternary complexes formed by the polymerase and next correct nucleotide on the reversibly terminated, immobilized primer-template hybrids, and (iii) activation: cleaving the reversible terminator from the extended primers. Each cycle resulted in addition of a single nucleotide and detection of a subsequent nucleotide position. As such the number of cycles correlated directly with the length of the sequence read for each bead.

The sequencing cycle was initiated by polymerase catalyzed incorporation of reversible terminator nucleotides at the 3'-ends of the primers of the immobilized primer-template hybrids by contacting the hybrids with unlabeled reversibly terminated nucleotide analogs of dATP, dGTP, dCTP, and dTTP) in the presence of polymerase (M15 polymerase or Therminator™ polymerase, respectively). The reversible terminator nucleotide used included a 3'-ONH$_2$ reversible terminator moiety. A description of this reversible terminator nucleotide can be found in U.S. Pat. No. 7,544,794, which is incorporated herein by reference.

dNTPs were removed from the solution and the flow cell was washed using a solution containing isopropanol, Tween-80, hydroxylamine and EDTA. However, the polymerase was not removed with the dNTPs and remained in the flow cell.

The cycle then continued with an examination step in which each of four different nucleotides was individually delivered to the flow cell (Cy5 labeled dTTP, Cy5 labelled dATP, Cy5 labeled dCTP and Cy5 labeled dGTP, respectively). The polymerase was present in the flow cell during this step having been retained from the previous step. Formation of ternary complexes occurred and free nucleotide was removed from the flow cell by delivery of reagent including LiCl, betaine, Tween-80, KCl, Ammonium Sulfate, hydroxylamine, and EDTA. The reagent stabilized ternary complexes while free nucleotides were removed from the flow cell. The flow cell was then examined for ternary complex formation at the immobilized primer-template hybrids. The flow cell was imaged via fluorescence microscopy to detect ternary complexes that contained a labeled nucleotide that was a cognate for the next correct nucleotide in each of the template nucleic acids. Reversible terminator moieties on the 3' nucleotides of the primer strands precluded nucleotide incorporation during the ternary complex formation and detection steps.

Following the examination step, a wash was carried out to clear the flow cell of the nucleotides from the examination subroutine. Then the sequencing cycle continued with a step in which the reversible terminator moieties were removed from the primers using sodium acetate and sodium nitrite as set forth in U.S. Pat. No. 7,544,794, which is incorporated herein by reference. The flow cell was then washed. Polymerase from the examination steps was then removed. The sequencing process then proceeded to the next nucleotide position by returning to the first step of the next cycle where a reversibly terminated nucleotide is added to the primers of the immobilized template strands.

Figure 3:
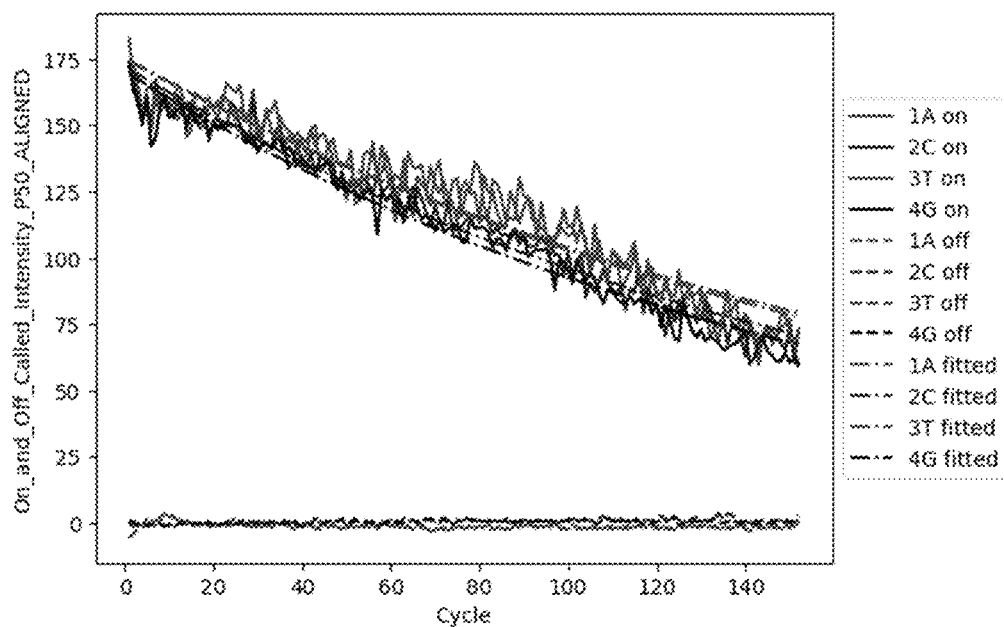
FIG. 3 is a graph showing signal intensity vs. sequencing cycle for the M15 polymerase.
Figure 4:
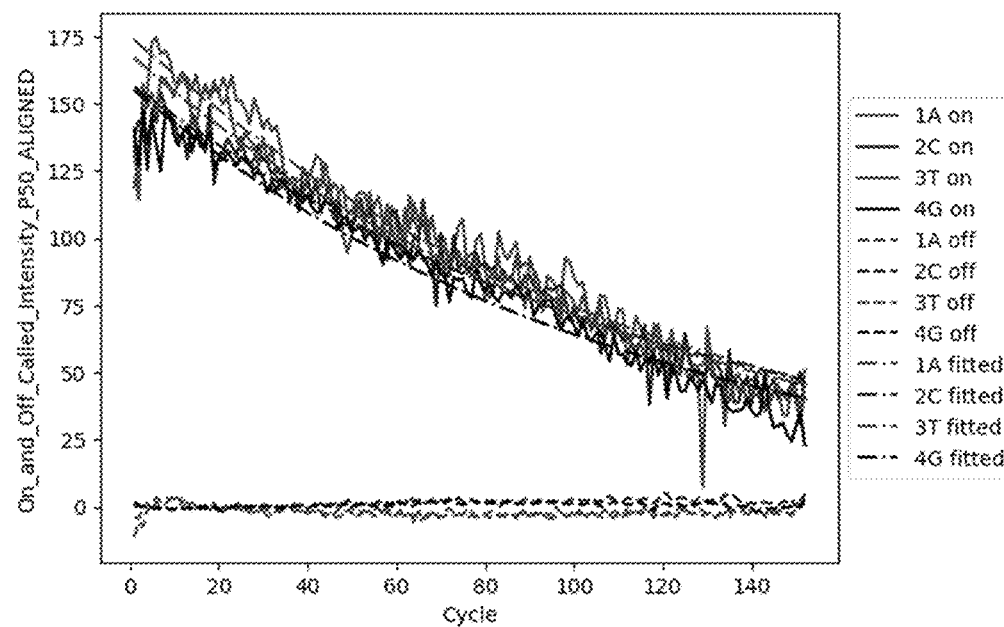
FIG. 4 is a graph showing signal intensity vs. sequencing cycle for the Therminator™ polymerase.

Results:

FIG. 3 is a graph showing a plot of signal intensity vs. sequencing cycle for sequencing using the M15 polymerase. FIG. 4 is a graph showing a plot of signal intensity vs. sequencing cycle for sequencing using the Therminator™ polymerase. Individual traces are shown for the 'on' intensity detected for each nucleotide type and for the 'off' intensity for each nucleotide type. For each bead in each cycle, the nucleotide type that produced the highest signal was identified as the 'on' signal and the other three nucleotide types were identified as the 'off' signal. The 'on' signals for each nucleotide type were averaged across all bead types detected in a given cycle, and the median intensity was plotted across all cycles to obtain each of the 'on' signal traces shown in FIGS. 3 and 4 as straight lines. Similar averaging of signal intensities across all bead types on a per cycle basis was used to arrive at the 'off' intensity traces shown in FIGS. 3 and 4 as dashed lines.

Signal decay for the 'on' traces was evaluated by fitting the traces to a curve defined by the following equation:

$$I=I_0 e^{-(n/\tau)}$$

wherein I is signal intensity, n is the number of cycles and $\tau$ is the cycle when the signal is about 37% of $I_0$ (initial signal intensity). The lines that are fitted to the 'on' signals are shown in the plots of FIG. 3 and FIG. 4 as dash-dotted lines. Higher $\tau$ is indicative of reduced rate of signal decay, which is generally preferred since it indicates increased read length and sequencing accuracy, whereas increased rate of signal decay is characterized by lower values for $\tau$. The potential for longer read length is also indicated by the magnitude of the separation between the on signals and off signals, where a higher separation indicates longer read length potential for the run. The run performed with M15 polymerase yielded a separation metric of 54.39 at the end of the run (i.e. cycle 150) which was nearly 5 fold higher than the separation metric of 11.03 measured at the end of the run performed with Therminator™ polymerase. Accordingly, the M15 polymerase showed longer read length potential than Therminator™ polymerase.

In nucleic acid sequencing applications, the Q score is a property that is logarithmically related to the base calling error probabilities (P) according to the following equation $$Q=-10 \log(P)$$

For example, a Q score of 20 (Q20) for a particular base call is equivalent to a 1 in 100 probability that the base call is incorrect. This means that the base call accuracy (i.e., the probability of a correct base call) is 99.0%. A higher base call accuracy of 99.9% is indicated by a Q score of Q30 and indicates an incorrect base call probability of 1 in 1000. Q40 indicates a base call accuracy of 99.99% (i.e. incorrect base call probability of 1 in 10,000), Q50 indicates an even higher base call accuracy of 99.999% (i.e. incorrect base call probability of 1 in 100,000), and so on. Currently available high throughput sequencing platforms (i.e., "next generation" sequencing platforms such as those available from Illumina, Inc., San Diego Calif.) typically use Q30 as a benchmark for quality. Higher Q scores are indicative of increased accuracy of variant calls, which provides increased accuracy of conclusions and reduced costs for validation experiments.

When sequencing was carried out using M15 polymerase a Q score of Q70 was obtained without discarding any of the observed data. By comparison, the sequencing run that used Therminator™ polymerase produced a Q score of 51 without discarding any data. Even when the lowest quality of the sequencing data (i.e., 30% of the data) was omitted from the analysis, the Therminator™ polymerase did not achieve a Q score higher than Q55. Accordingly, the use of M15 polymerase for nucleic acid sequencing resulted in more accurate sequencing than the results obtained using Therminator™ polymerase in the same sequencing protocol.

What is claimed is:

1. A method of identifying a base in a primed template nucleic acid, comprising
   (a) contacting a primer-template nucleic acid hybrid with an engineered polymerase comprising a variant of SEQ ID NO:1, the variant being at least 90% identical to SEQ ID NO:1 and comprising amino acid substitutions L408F, Y409F and P410T or amino acid substitutions L408F, Y409H and P410V and a test nucleotide, thereby forming a ternary complex, wherein the engineered DNA polymerase has increased accuracy in pairing nucleotides to template bases as compared to a control polymerase having an amino acid sequence of SEQ ID NO:1;
   (b) detecting the complex without incorporation of the test nucleotide into the primer;
   (c) identifying the next base of the primed template nucleic acid from the detected complex; and
   (d) incorporating into the primer a nucleotide that is complementary to the next template base, wherein the polymerase used to catalyze incorporation is a different polymerase from the engineered polymerase of steps (a)-(c).

2. The method of claim 1, wherein the contacting occurs under conditions that:
   stabilize the ternary complex formed between the polymerase, primer-template nucleic acid hybrid and test nucleotide when the test nucleotide is complementary to the next base of the primed template nucleic acid, and
   (ii) destabilize a binary complex formed between the primed template nucleic acid and the polymerase when the test nucleotide is not complementary to the next base of the primed template nucleic acid.

3. The method of claim 1, wherein the detecting comprises detecting a change in refractive index, a light scattering signal or a detectable tag.

4. The method of claim 1, wherein the nucleotide, polymerase or both comprise exogenous labels.

5. The method of claim 1, wherein the nucleotide comprises a reversible terminator.

6. A method of sequencing a template nucleic acid molecule, the method comprising
   (a) providing a template nucleic acid molecule primed with a primer;
   (b) contacting the primed template nucleic acid molecule with an engineered polymerase comprising a variant of SEQ ID NO:1, the variant being at least 90% identical to SEQ ID NO:1 and comprising amino acid substitutions L408F, Y409F and P410T or amino acid substitutions L408F, Y409H and P410V and at least one nucleotide molecule, wherein the engineered DNA polymerase has increased accuracy in pairing nucleotides to template bases as compared to a control polymerase having an amino acid sequence of SEQ ID NO:1;
   (c) identifying the nucleotide molecule without incorporation of the nucleotide molecule; and
   (d) incorporating the nucleotide into the primer using a different type of polymerase from the engineered polymerase of steps (a)-(c), thereby sequencing the template nucleic acid molecule.

7. The method of claim 1, wherein, in step (b), the primer comprises a blocking group at the 3' end of the primer to preclude incorporation of the test nucleotide.

8. A method of identifying a base in a primed template nucleic acid, comprising
   (a) contacting a primer-template nucleic acid hybrid with an engineered polymerase comprising a variant of SEQ ID NO:1, the variant being at least 90% identical to SEQ ID NO:1 and comprising amino acid substitutions L408F, Y409F and P410T or amino acid substitutions L408F, Y409H and P410V and a test nucleotide, thereby forming a ternary complex, wherein the engineered DNA polymerase has increased accuracy in pairing nucleotides to template bases as compared to a control polymerase having an amino acid sequence of SEQ ID NO:1;
   (b) detecting the complex without incorporation of the test nucleotide into the primer;
   (c) identifying the next base of the primed template nucleic acid from the detected complex; and
   (d) incorporating into the primer a nucleotide that is complementary to the next template base, wherein the nucleotide used for incorporation is a different nucleotide than the test nucleotide in steps (a)-(c).

9. The method of claim 8, wherein, in step (b), the primer comprises a blocking group at the 3' end of the primer to preclude incorporation of the test nucleotide.

10. The method of claim 8, wherein the contacting occurs under conditions that:
    stabilize the ternary complex formed between the polymerase, primer-template nucleic acid hybrid and test nucleotide when the test nucleotide is complementary to the next base of the primed template nucleic acid, and
    (ii) destabilize a binary complex formed between the primed template nucleic acid and the polymerase when the test nucleotide is not complementary to the next base of the primed template nucleic acid.

11. The method of claim 8, wherein the detecting comprises detecting a change in refractive index, a light scattering signal or a detectable tag.

12. The method of claim 8, wherein the nucleotide, polymerase or both comprise exogenous labels.

13. The method of claim 8, wherein the nucleotide comprises a reversible terminator.

14. The method of claim 8, wherein the incorporation step further comprises replacing the polymerase of steps (a)-(c) with a different type of polymerase that catalyzes the incorporation.

* * * * *

UNITED STATES PATENT AND TRADEMARK OFFICE
CERTIFICATE OF CORRECTION

PATENT NO. : 11,242,512 B2
APPLICATION NO. : 16/567476
DATED : February 8, 2022
INVENTOR(S) : Pinar Iyidogan Page 1 of 1

It is certified that error appears in the above-identified patent and that said Letters Patent is hereby corrected as shown below:

In the Claims

Claim 2, Column 63, Line 40:
Replace "stabilize the ternary complex formed between the poly-" with --(i) stabilize the ternary complex formed between the poly- --

Claim 10, Column 64, Line 54:
Replace "stabilize the ternary complex formed between the poly-" with --(i) stabilize the ternary complex formed between the poly- --

Signed and Sealed this
Tenth Day of May, 2022

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 775
<212> TYPE: PRT
<213> ORGANISM: artificial sequence
<220> FEATURE:
<223> OTHER INFORMATION: Synthetic Sequence

<400> SEQUENCE: 1

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300
```

```
Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720
```

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Lys Gln Val Gly Leu Gly Ala Trp
        755                 760                 765

Leu Lys Val Lys Gly Lys Lys
        770             775

<210> SEQ ID NO 2
<211> LENGTH: 774
<212> TYPE: PRT
<213> ORGANISM: artificial sequence
<220> FEATURE:
<223> OTHER INFORMATION: synthetic construct

<400> SEQUENCE: 2

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

```
Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
                515                 520                 525

Glu Glu Lys Tyr Gly Phe Lys Val Ile Tyr Ser Asp Thr Asp Gly Phe
                530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
                690                 695                 700

Lys Gly Ser Gly Arg Ile Gly Asp Arg Ala Ile Pro Phe Asp Glu Phe
705                 710                 715                 720
```

```
Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
        740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 3
<211> LENGTH: 773
<212> TYPE: PRT
<213> ORGANISM: artificial sequence
<220> FEATURE:
<223> OTHER INFORMATION: synthetic construct

<400> SEQUENCE: 3

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300
```

```
Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
            325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Tyr
        370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
            515                 520                 525

Glu Glu Lys Phe Gly Phe Lys Val Leu Tyr Ala Asp Thr Asp Gly Phe
        530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720
```

```
Asp Pro Ala Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
            755                 760                 765

Leu Lys Pro Lys Thr
            770

<210> SEQ ID NO 4
<211> LENGTH: 784
<212> TYPE: PRT
<213> ORGANISM: artificial sequence
<220> FEATURE:
<223> OTHER INFORMATION: synthetic construct

<400> SEQUENCE: 4

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300
```

-continued

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Phe Phe Thr Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

-continued

```
Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys Val Asp Leu Gln Pro Ser Leu Ile Ser
770             775                 780
```